United States Patent
Ratan et al.

(10) Patent No.: US 10,716,783 B2
(45) Date of Patent: Jul. 21, 2020

(54) PROLYLHYDROXYLASE/ATF4 INHIBITORS AND METHODS OF USE FOR TREATING NEURAL CELL INJURY OR DEATH AND CONDITIONS RESULTING THEREFROM

(71) Applicant: CORNELL UNIVERSITY, Ithaca, NY (US)

(72) Inventors: Rajiv R. Ratan, Scarsdale, NY (US); Saravanan S. Karuppagounder, White Plains, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/104,012

(22) PCT Filed: Dec. 12, 2014

(86) PCT No.: PCT/US2014/070052
§ 371 (c)(1),
(2) Date: Jun. 13, 2016

(87) PCT Pub. No.: WO2015/089416
PCT Pub. Date: Jun. 18, 2015

(65) Prior Publication Data
US 2016/0317526 A1 Nov. 3, 2016

Related U.S. Application Data

(60) Provisional application No. 61/915,068, filed on Dec. 12, 2013.

(51) Int. Cl.
*A61K 31/47* (2006.01)
*A61K 31/4709* (2006.01)

(52) U.S. Cl.
CPC .......... *A61K 31/4709* (2013.01); *A61K 31/47* (2013.01)

(58) Field of Classification Search
CPC .............................. A61K 31/47; A61K 31/4709
See application file for complete search history.

(56) References Cited

U.S. PATENT DOCUMENTS

| | | | |
|---|---|---|---|
| 2003/0176317 A1* | 9/2003 | Guenzler-Pukall | A61K 31/00 514/1 |
| 2007/0203079 A1* | 8/2007 | Caldwell | A61K 31/00 514/27 |
| 2009/0047294 A1 | 2/2009 | Carmeliet et al. | |
| 2011/0286927 A1 | 11/2011 | Ratan | |
| 2012/0034599 A1 | 2/2012 | Wechsler et al. | |
| 2013/0023528 A1 | 1/2013 | Ratan et al. | |
| 2013/0224169 A1* | 8/2013 | Ford, Jr. | A61K 31/14 424/94.1 |
| 2014/0081601 A1* | 3/2014 | Zhang | A42C 2/00 703/1 |
| 2014/0163328 A1* | 6/2014 | Geva et al. | A61B 5/048 600/300 |

FOREIGN PATENT DOCUMENTS

| | | | |
|---|---|---|---|
| WO | WO2007/070359 A2 | 6/2007 | |
| WO | WO 2008/014602 A1 | 2/2008 | |
| WO | WO 2011106226 A2 * | 9/2011 | ........... A61K 31/404 |
| WO | WO 2011/137511 A1 | 11/2011 | |

OTHER PUBLICATIONS

Kushner, "Concussion in Sports: Minimizing the Risk for Complications", American Family Physician, 2001, American Academy of Family Physicians, vol. 64(6), pp. 1007-1014.*
Abdul-Muneer et. al., Free Radical Biology & Medicine, Mar. 2013, Elsevier, vol. 60, pp. 282-291 (Year: 2013).*
Rosenfeld et. al., Injury, 2010, Elsevier, vol. 41, pp. 437-443 (Year: 2010).*
Vachal et. al., Journal of Medicinal Chemistry, 2012, American Chemical Society, vol. 55, pp. 2945-2959 (Year: 2012).*
Smirnova, N.A. et al., "Utilization of an In Vivo Reporter for High Throughput Identification of Branched Small Molecule Regulators of Hypoxic Adaptation", Chemistry & Biology, (Apr. 23, 2010), vol. 17, pp. 380-391.
Supplementary European Search Report dated May 9. 2017 issued in corresponding European Patent Application No. 14869532.3.
Ameri, K. et al., "Anoxic induction of ATF-4 through HIF-1-indepenent pathways of protein stabilization in human cancer cells", Blood, (Mar. 1, 2004), vol. 103, No. 5, pp. 1876-1882.
Karuppagounder, S.S. et al., "Hypoxia-inducible factor prolyl hydroxylase inhibition: robust new target or another big bust for stroke therapeutics?", Journal of Cerebral Blood Flow & Metabolism, (2012), vol. 32, pp. 1347-1361.
McDonough, M.A. et al., Cellular oxygen sensing: Crystal structure of hypoxia-inducible factor prolyl hydroxylase (PHD2), PNAS, (Jun. 27, 2006), vol. 103, No. 26, pp. 9814-9819.

(Continued)

*Primary Examiner* — Sarah Pihonak
(74) *Attorney, Agent, or Firm* — Scully, Scott, Murphy & Presser, P.C.

(57) ABSTRACT

Methods for treating a patient suffering from neural cell injury, the method comprising administering to the patient an effective amount of a HIF prolyl-4-hydroxylase inhibiting compound having the following general formula (1) wherein $R^1$ is a cyclic group containing at least three and up to seven carbon atoms and optionally containing one or more heteroatoms selected from O, N, and S, and optionally attached to the shown carbon atom by a linking group; $R^2$ is independently selected from said cyclic groups of $R^1$ and acyclic hydrocarbon groups $R^5$ containing up to twenty carbon atoms; $R^3$ is selected from hydrogen atom and hydrocarbon groups containing up to six carbon atoms; $R^6$ and $R^7$ are independently selected from hydrogen atom, hydrocarbon groups containing up to three carbon atoms, halogen atom, and polar groups, as well as methylene-linked versions thereof; and t is 0 or 1.

9 Claims, 23 Drawing Sheets
(23 of 23 Drawing Sheet(s) Filed in Color)

(56) References Cited

OTHER PUBLICATIONS

Singh, N. et al., "Hypoxia inducible factor-1: its potential role in cerebral ischemia", Cellular and Molecular Neurobiology, (2012), vol. 32, No. 4, pp. 491-507.
International Search Report dated Mar. 11, 2016 issued in PCT/US14//0052.
Prince, C. et al., "Evaluation and Treatment of Mild Traumatic Brain Injury: The Role of Neuropsychology", Brain Sci. 2017, 7, 105, pp. 1-14.
Katz, D.I. et al., "Mild Traumatic brain injury", Handbook of Clinical Neurology, (2015), Vol. 127, (3rd series), Traumatic Brain Injury, Part I, pp. 131-156.
Prince, C. et al., "Evaluation and Treatment of Mild Traumatic Brain Injury: The Role of Neuropsychology", Brain Sci. 7, 105, pp. 1-14.

\* cited by examiner

PROLYLHYDROXYLASE/ATF4 INHIBITORS AND METHODS OF USE FOR TREATING NEURAL CELL INJURY OR DEATH AND CONDITIONS RESULTING THEREFROM

CROSS REFERENCE TO RELATED APPLICATION

This application claims the benefit of priority from U.S. Provisional Application No. 61/915,068, filed on Dec. 12, 2013.

FIELD OF THE INVENTION

The invention relates generally to methods for treating neural cell injury or death (e.g., brain and spinal cord injury), and more particularly, methods that include administering to a subject with such injury an inhibitor of hypoxia inducible factor (HIF) prolyl-4-hydroxylases (PHDs) and/or inhibitor of ATF4. The invention is also directed to particular compounds and pharmaceutical compositions useful in treating neural cell injury and conditions or diseases caused thereby or resulting therefrom.

BACKGROUND OF THE INVENTION

Brain or spinal cord injury is associated with significant morbidity and mortality and can occur as a result of, for example, intracerebral hemorrhage (ICH), stroke, traumatic brain injury, brain tumors, arterio-venous malformations, amyloid angiopathy, anticoagulant use, or sickle cell disease. Brain injury resulting from ICH is particularly prevalent, with a worldwide incidence of 10-20 cases per 100,000 people. As therapies targeted at reducing primary injury have been largely unsuccessful, there has been a renewed focus on secondary injury mechanisms. In particular, blood breakdown products in the brain after ICH appear to be an important source of secondary injury. Specifically, functional impairment is associated with red blood cell lysis, release of heme, and increases in redox active iron. In this scheme, free iron is able to interact with peroxide to generate highly reactive hydroxyl radicals via Fenton Chemistry and oxidative damage to lipid, protein and DNA in diverse cell types.

A class of metalloenzymes that has been implicated in neuronal survival in vitro and in vivo is a family of oxygen sensors known as the hypoxia inducible factor prolyl hydroxylase domain enzymes (HIF PHDs). These oxygen, 2-oxoglutarate, and iron-dependent dioxygenases destabilize the transcriptional activator, HIF-1α under normoxia. Iron chelators are known to inhibit the HIF prolyl hydroxylases in normoxia, thus inhibiting oxygen-dependent hydroxylation of HIF, its recruitment of VHL, and its proteosomal degradation. Iron chelators have also been shown to stabilize HIF-1 and activate a suite of putative adaptive genes at concentrations where they protect neurons from oxidative death.

Although chelation of iron has its benefits, there would be a greater benefit in preventing hemin-induced neuronal death by targeting HIF PHDs rather than free iron. Nevertheless, until now, such a methodology has remained elusive.

SUMMARY OF THE INVENTION

The instant disclosure is foremost directed to a method for treating neural cell injury (e.g., brain or spinal cord injury) in a subject by administering to the subject an effective amount of a quinoline-based HIF PHD-inhibiting compound having the following chemical structure:

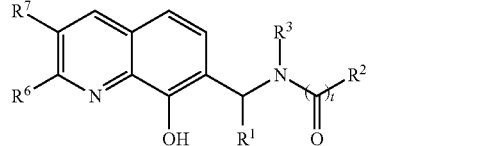

(1)

In Formula (1), $R^1$ is a cyclic group containing at least three and up to seven ring carbon atoms and optionally containing one or more ring heteroatoms selected from O, N, and S, wherein said cyclic group is optionally substituted with one or more groups selected from —$R^4$, —C(O)$R^4$, —N$R^4{}_2$, —O$R^4$, NO$_2$, —C(O)N$R^4{}_2$, —N$R^4$C(O)$R^4$, —C(O)O$R^4$, —OC(O)$R^4$, —OC(O)N$R^4{}_2$, —N$R^4$C(O)N$R^4{}_2$, —N$R^4$C(O)O$R^4$, —SO$_2R^4$, nitrile, and halogen atom, wherein $R^4$ is, independently, hydrogen atom or acyclic hydrocarbon group containing up to six carbon atoms, and wherein said cyclic group is optionally attached to the shown carbon atom by a linking group; $R^2$ is independently selected from said cyclic groups of $R^1$ and acyclic hydrocarbon groups $R^5$ containing up to twelve carbon atoms, wherein said cyclic group is optionally attached to the shown carbon or nitrogen atom by a linking group; $R^3$ is selected from hydrogen atom and hydrocarbon groups containing up to six carbon atoms, with $R^2$ and $R^3$ optionally interconnected; $R^6$ and $R^7$ are independently selected from hydrogen atom, hydrocarbon groups containing up to three carbon atoms, halogen atom, and polar groups selected from —C(O)$R^4$, —N$R^4{}_2$, —O$R^4$, —NO$_2$, —C(O)N$R^4{}_2$, —N$R^4$C(O)$R^4$, —C(O)O$R^4$, —OC(O)$R^4$, —OC(O)N$R^4{}_2$, —N$R^4$C(O)N$R^4{}_2$, —N$R^4$C(O)O$R^4$, —SO$_2R^4$, and nitrile, as well as methylene-linked versions thereof; and t is 0 or 1.

BRIEF DESCRIPTION OF THE FIGURES

The patent or application file contains at least one drawing executed in color. Copies of this paper or patent application publication with color drawing(s) will be provided by the Office upon request and payment of the necessary fee.

FIG. 1A: Desferoxamine, a canonical HIF PHD inhibitor abrogates hemin toxicity in primary cortical neurons ($EC_{50}$=34.1 micromolar as measured by MTT assay; see FIGS. 1E, 1I for LIVE/DEAD assay, DFO=100 micromolar); hippocampal neuroblasts ($EC_{50}$=50.8 micromolar as measured by MTT assay), and immortalized striatal neuroblasts (26.7 micromolar as measured by MTT assay). FIG. 1B: Cyclopriox, a HIF PHD inhibitor structurally diverse from DFO, also abrogates hemin-induced toxicity in primary cortical neurons ($EC_{50}$=1.4 micromolar as measured by MTT assay; see FIGS. 1F, 1J for LIVE/DEAD assay, CPO=3 micromolar). FIG. 1C: DHB, a structurally diverse HIF PHD inhibitor that does not bind iron abrogates hemin toxicity in primary cortical neurons ($EC_{50}$=34.9 micromolar) as measured by MTT assay; see FIGS. 1G, 1K for LIVE/DEAD assay, DHB=100 micromolar); hippocampal neuroblasts ($EC_{50}$=86.7 micromolar as measured by MTT assay), and immortalized striatal neuroblasts (219.6 micromolar). FIG. 1L: Western blot confirming that DFO, DHB, and CPO, all established HIF PHD inhibitors, stabilize HIF-1 protein in primary neurons.

FIGS. 1M, and 1O-1R: Cyclopirox prevents hemin-induced death (FIG. 1Q) but cyclopirox analog without HIF PHD inhibitory activity does not (FIG. 1R). FIG. 1N: Protection by cyclopirox is not associated with significant (p>0.05) reductions in total iron as measured by mass spectrometry. These results establish HIF PHD inhibitory activity as the on target effector of cyclopirox protection and not the binding of free iron.

FIGS. 2A and 2B: Scheme for selectively reducing PHD 1, 2, and 3 in the striatum of adult mice. FIGS. 2C-2F: Triple floxed PHD mice were injected with AAV8-Cre Recombinase into the striatum of mice. Effective recombination was verified using Td-Tomato Floxed reporter line (FIG. 2C), and sectioning revealed reporter expression which is highest at those coordinates corresponding to subsequent collagenase injection and hemorrhagic stroke (FIG. 2D). FIG. 2E: Quantitative PCR confirms reduction in PHD1, PHD2 and PHD3 expression in vivo in the striatum. As expected, reductions in PHD expression lead to increases in VEGF and Epo expression in the striatum-known HIF dependent genes. FIGS. 2G, 2H. Conditional reduction of HIF PHDs enhances functional recovery from ICH in mice using a corner task (spatial neglect task) and tape removal task (sensory neglect).

FIG. 3A: In silico modeling identifies the ability of adaptoquin to fit into the active site of HIF PHDs. FIG. 3B: Adpatoquin inhibits activity of recombinant HIF PHD2 as assayed by non-denaturing mass spectrometry of a HIF peptide. Under steady state conditions, activity of HIF PHD2 with its co-substrate 2-oxoglutarate involves two peaks that represent non-hydroxylated and hydroxylated peptide. The hydroxylated peptide disappears in the presence of HIF PHD2 inhibition by adaptoquin. FIG. 3C: Adaptoquin inhibits the HIF PHDs in brain in a dose dependent fashion as monitored in ODD-luciferase reporter mice via in vivo bioluminescence imaging. The reporter contains the ODD domain of HIF-1 which confers HIF PHD regulated stability on it. It is expressed in all cells of the body, but is destabilized in the absence of HIF PHD inhibition and stabilized in its presence. Quantitative measurements confirm stability of the ODD-luc in brain, kidney and liver (FIGS. 3D and 3E.). To verify that the reporter activity is increased in the brain, the reporter activity was monitored in lysates from different brain regions and found dose dependent increases throughout the brain. Similar results were seen in the kidney and liver.

FIGS. 4A-4N. Adaptoquin delivered post-injury reduces cell death and enhances functional recovery post injury in mice and rats. Adaptoquin's effects in mice are not associated with global shifts of iron out of the brain. FIG. 4A: Experimental design for schedule of delivery of adaptaquin post-ICH. 30 mg/kg was delivered post-injury and then daily for seven days during which behavioral analysis was done. Mice were sacrificed at day 7 for qPCR and Fluoro-jade staining. FIG. 4B: Adaptoquin induced p21 expression a gene known to be induced by HIF PHD inhibition in neurons. FIGS. 4C, 4D: Adaptoquin corrects behavioral deficits associated with ICH including the corner task (spatial neglect) and tape removal task (sensory neglect). FIG. 4L: Protocol for evaluating the total concentrations of iron and zinc in brain following ICH in vehicle and adaptoquin treated mice. FIGS. 4M, 4N: Pseudocolored sections of collagenase induced ICH in mice after 7 days. Note that total iron and zinc do not change in the CNS qualitatively or quantitatively. These studies are consistent with the notion that adaptoquin works by inhibiting a specific metalloenzyme rather than global movement of metal ions.

FIG. 5A shows that 1 micromolar adaptaquin can be added up to 16 hours after treatment with the glutamate analog, homocysteate, and protect neurons. FIG. 5B shows that this protection is significant using the LIVE/DEAD stain. To determine the mechanism of adaptoquin, transcriptomic experiments were performed using non-protective and protective concentrations of drug harvesting RNA just prior to the time the cell's becoming insensitive to adaptoquin (16 hrs), as provided in FIG. 5C. The results show that adaptoquin normalizes the same gene cassette at 0.1 micromolar as 1 micromolar, but the level of modulation of those genes is greater at the protective concentration (FIGS. D, E, F). Transcription factor analysis demonstrated that ATF-4 regulated genes were significantly represented in the group modulated by adaptoquin. The results also confirmed downregulation of ATF4 dependent genes induced by oxidative stress and previously shown to be associated with death in these cells.

FIG. 6C shows that adaptoquin abrogates oxidative stress induced ATF4 occupancy at the promoter of Trib3. FIGS. 6D, 6E show that daptoquin can directly modulate ATF4 dependent death at concentrations protective in the oxidative stress model. Expression of ATF4 was forced into primary neurons, which induces death of these neurons by MTT assay (FIG. 6D) or LIVE/DEAD staining, Green is live, Red is dead (FIG. 6E). Adaptoquin also mitigates death induced by oxidative stress and ATF4 forced expression. FIG. 6F shows that mutation of conserved prolines in the C-terminal residue of ATF4, which are candidate hydroxylation sites, abrogates death seen with wt ATF4. FIG. 6G shows that adaptoquin inhibits ATF4 hydroxylation as monitored by a ATF4 immunoprecipitation followed by immunoblotting with an antibody that recognizes hydroxylated prolines. FIG. 6H, 6I shows that, consistent with the notion that protection is HIF independent, adaptoquin stabilizes HIF-1 at concentrations higher than that required for full protection.

DETAILED DESCRIPTION OF THE INVENTION

Figures 1A, 1B, 1C:
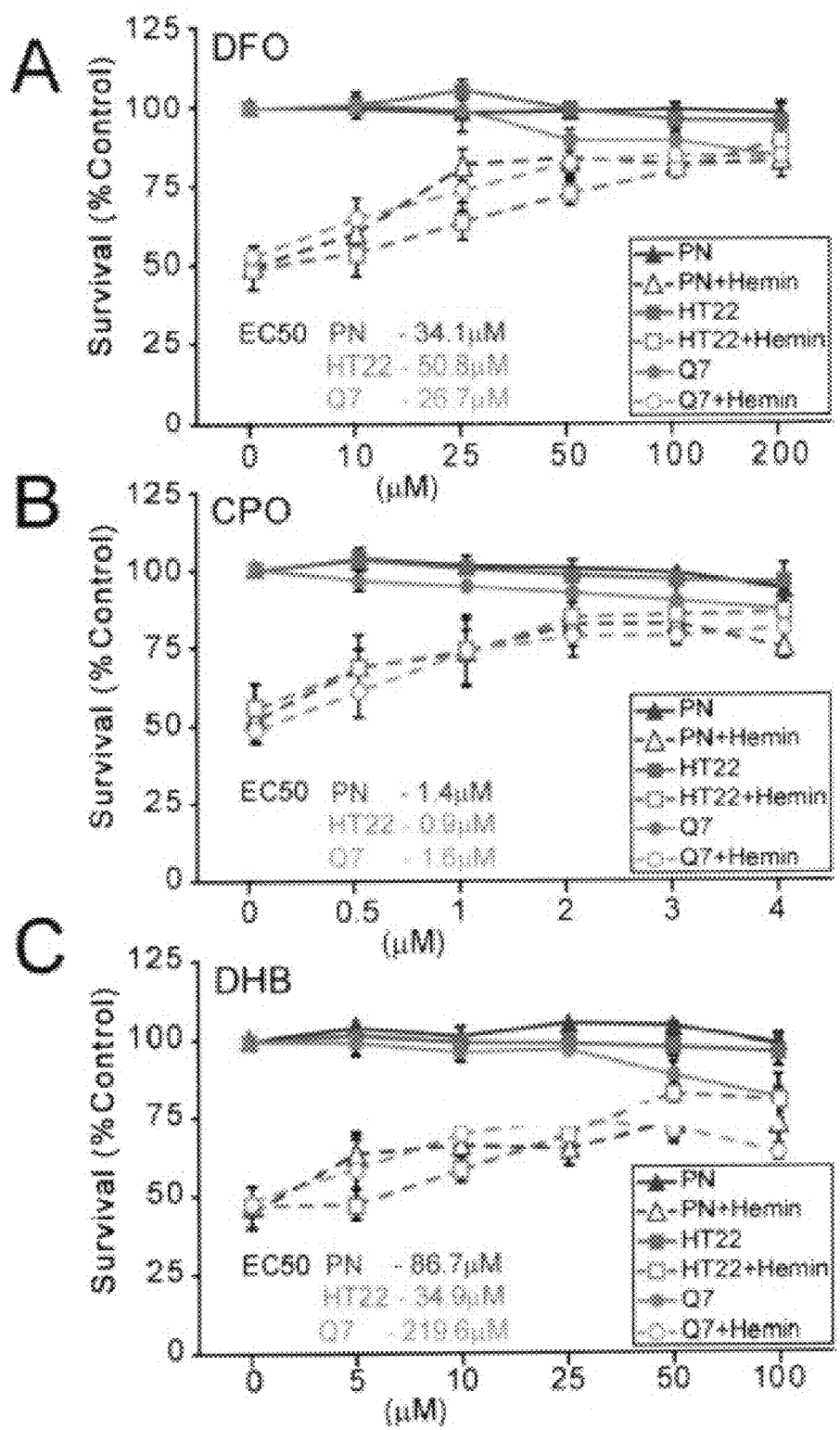
FIGS. 1A-1L: Structurally diverse HIF PHD inhibitors stabilize HIF-1 and abrogate toxicity induced by hemin, a byproduct of blood breakdown, in cortical neurons hippocampal neuroblasts and striatal neuroblasts (not shown).
Figures 1D, 1E, 1F, 1G, 1H, 1I, 1J, 1K:
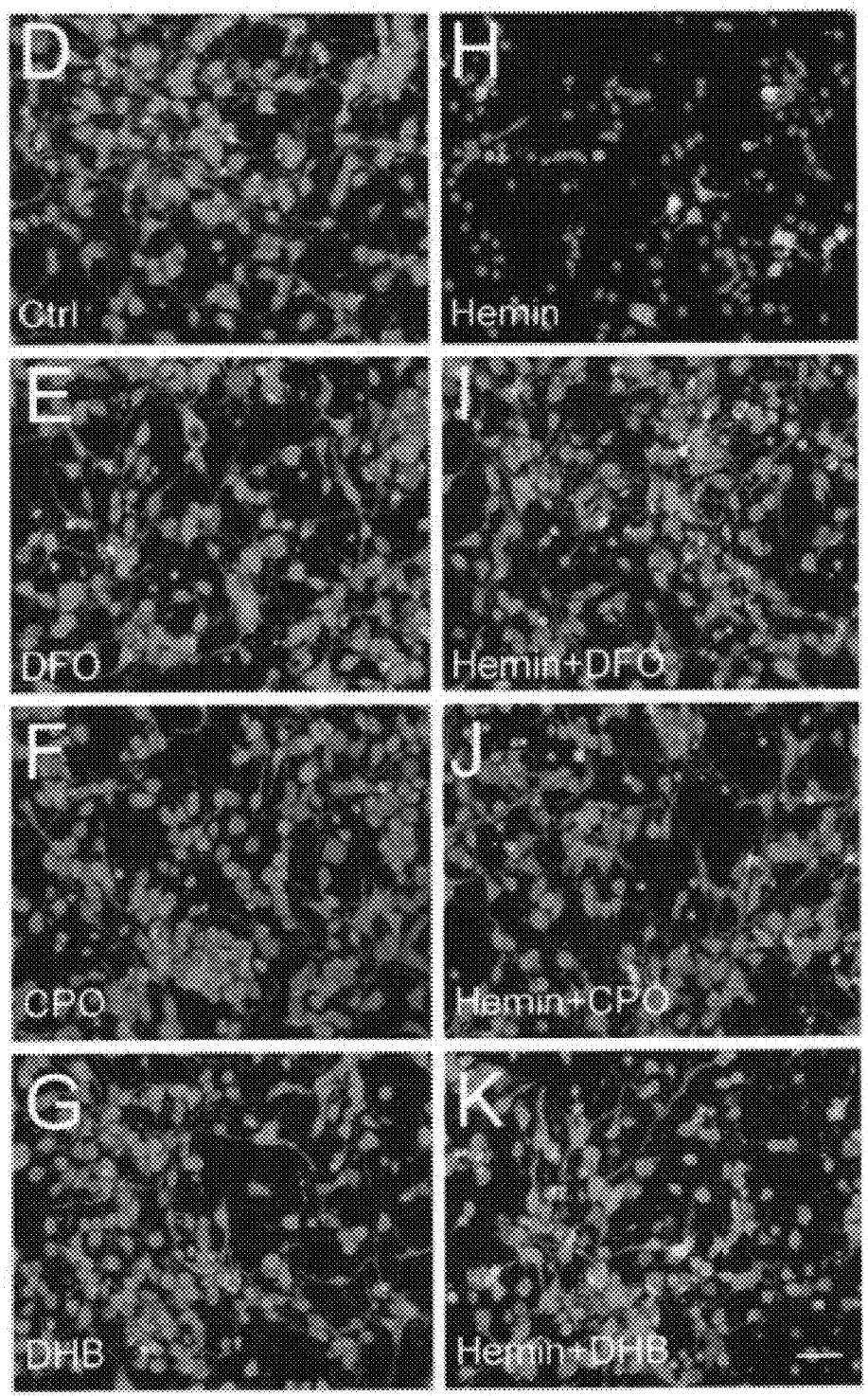
Figures 1L, 1M, 1N, 1O, 1P, 1Q, 1R:
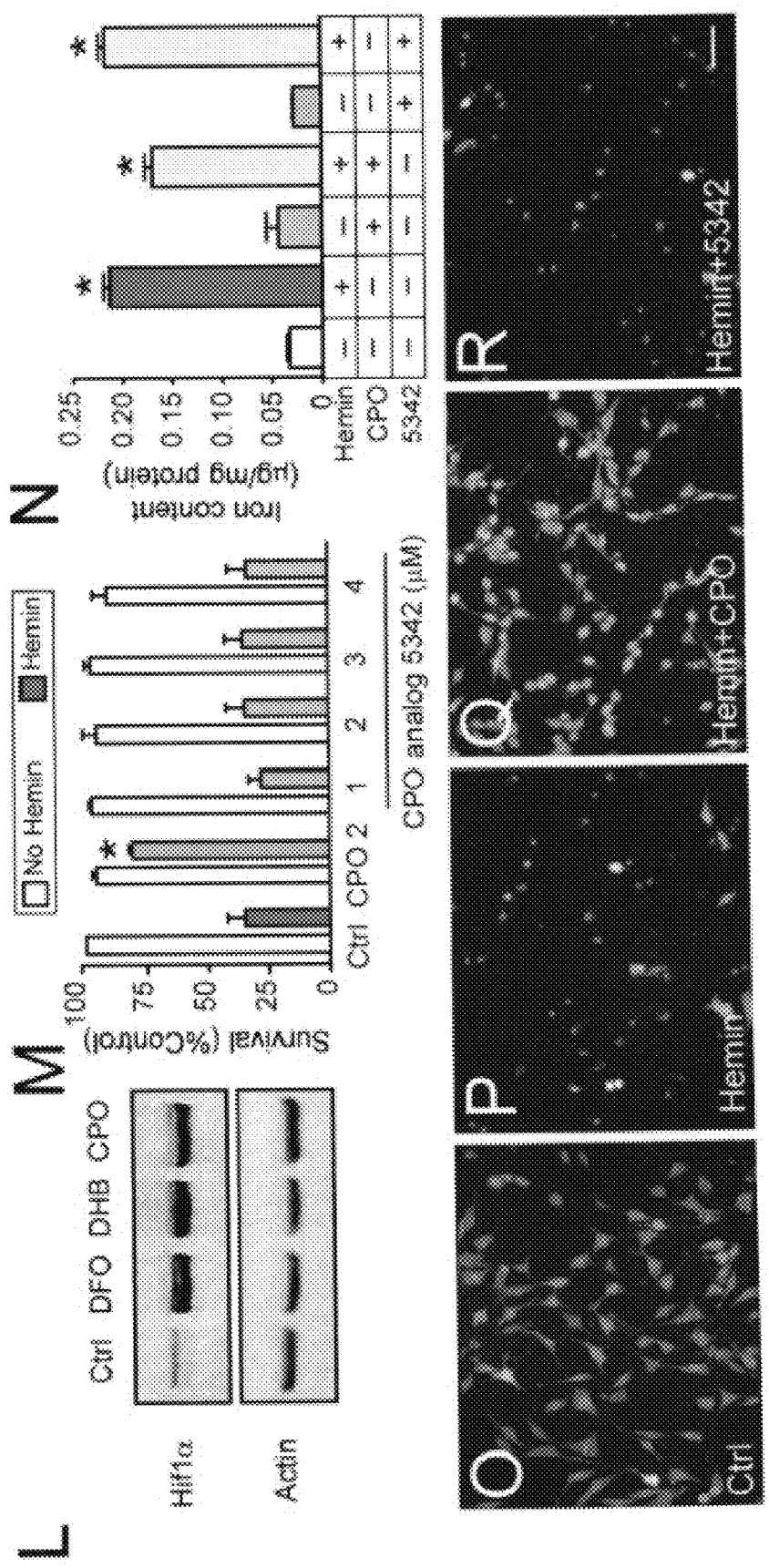
FIGS. 1M-1R: Structure activity studies of cyclopirox reveal that an analog of cyclopirox which possess iron chelating activity but no HIF PHD inhibitory activity loses its ability to prevent hemin induced death. Moreover, protective concentrations of cyclopirox fail to significantly reduce iron content in neurons.
Figures 2A, 2B:
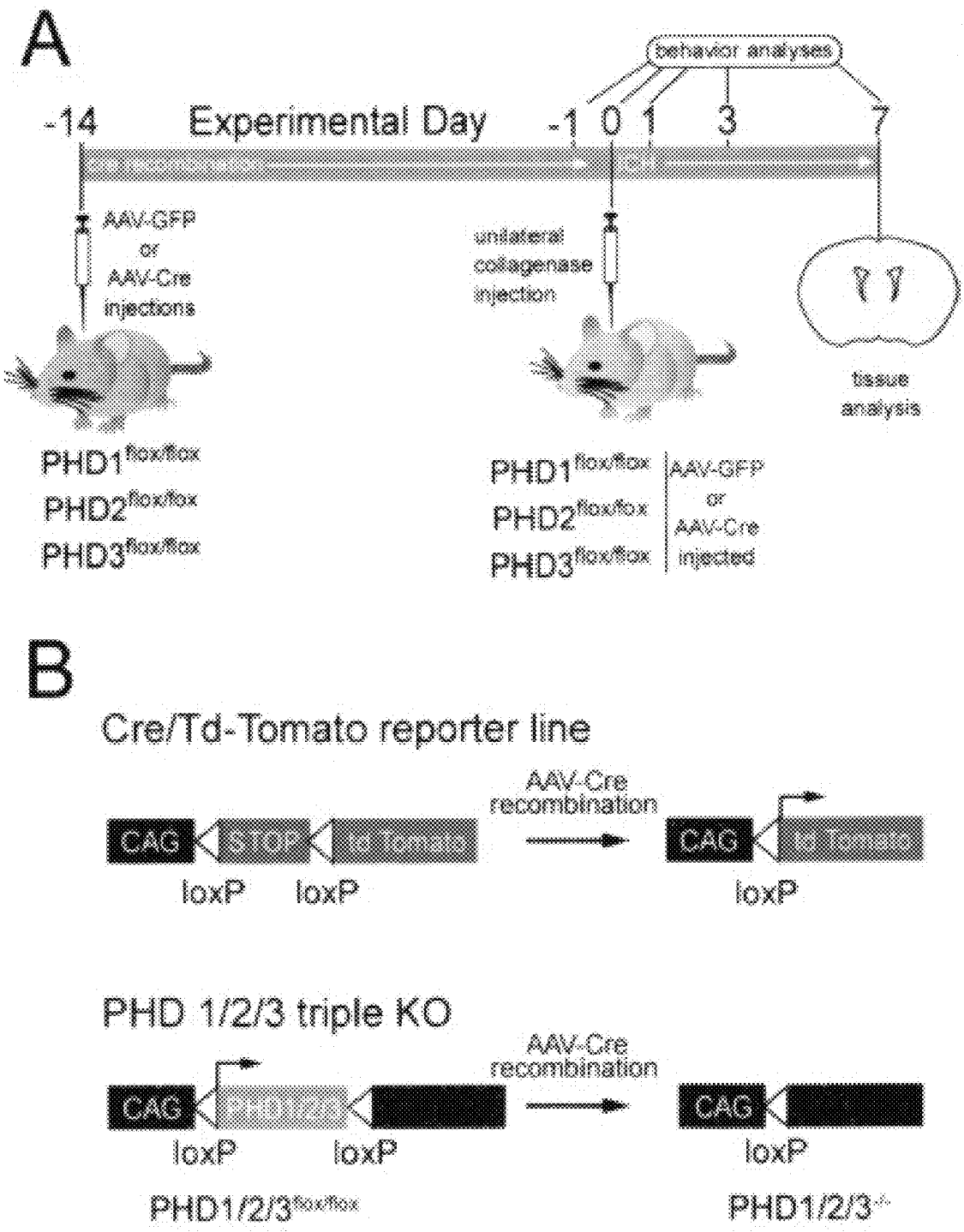
FIGS. 2A-2H: Molecular reduction of all three HIF PHD isoforms in the striatum of mice enhances functional recovery following brain hemorrhage.
Figures 2C, 2D:
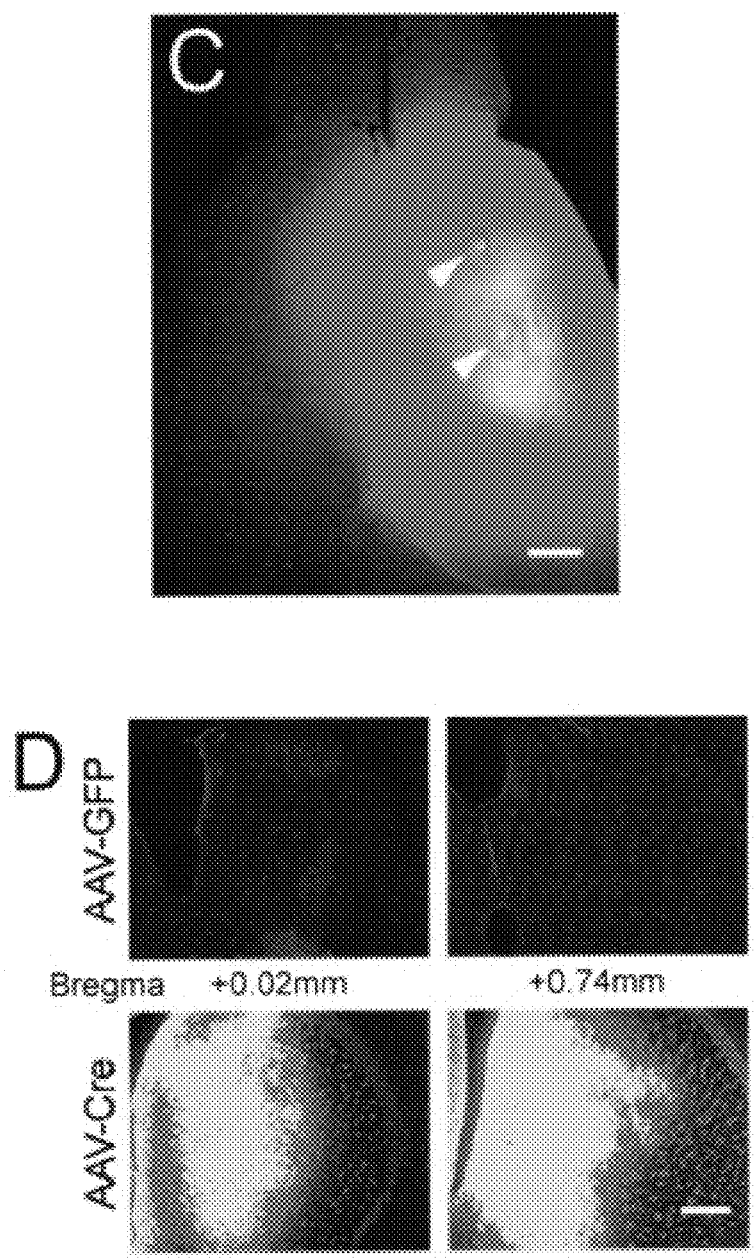
Figure 2E:
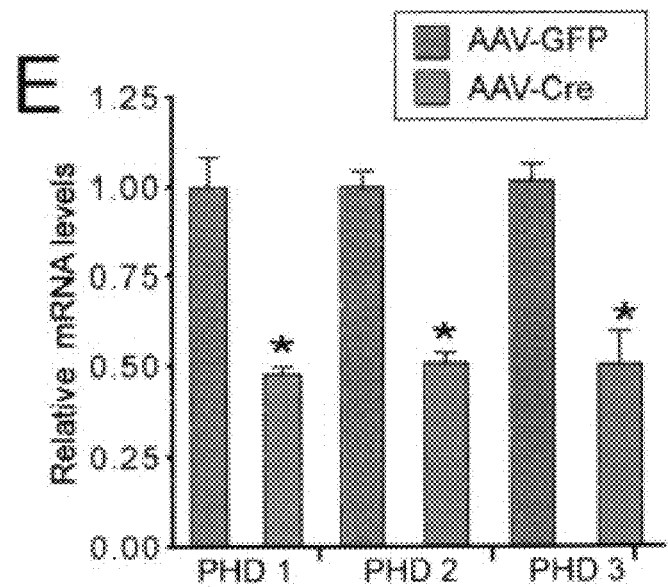
Figure 2F:
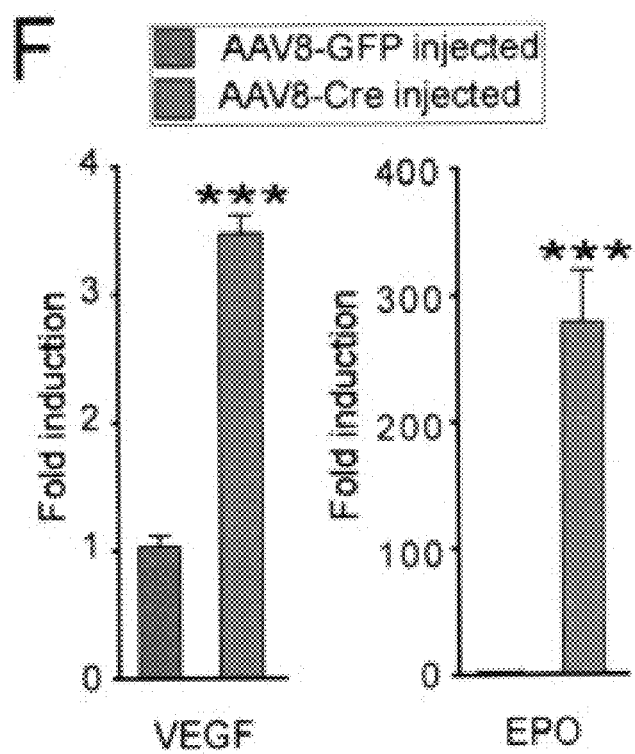
Figure 2G:
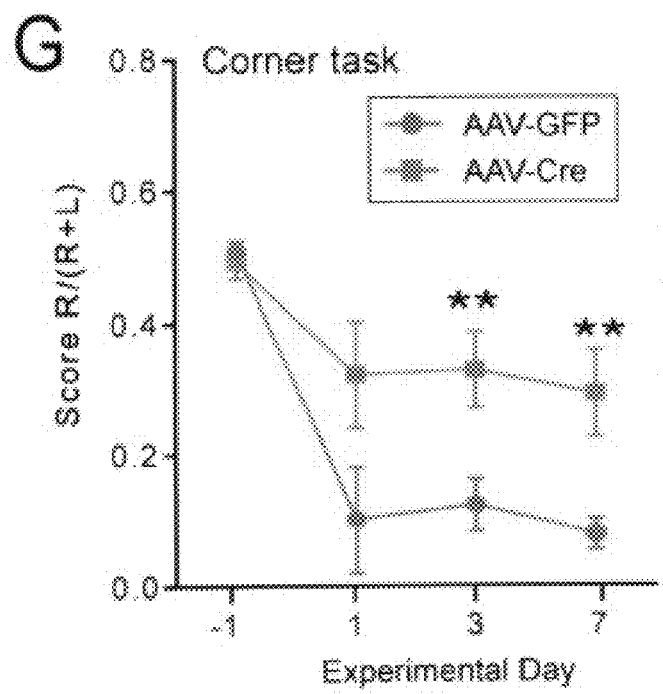
Figure 2H:
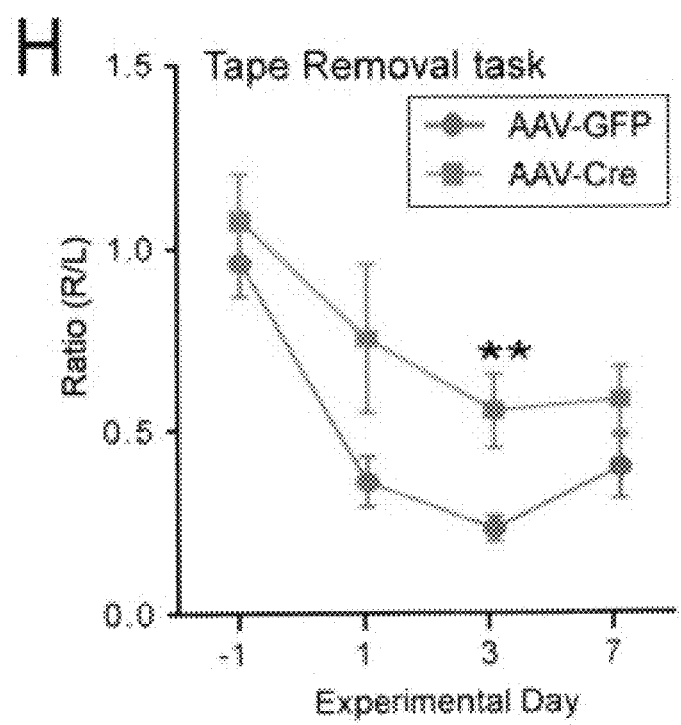
Figures 3A, 3B:
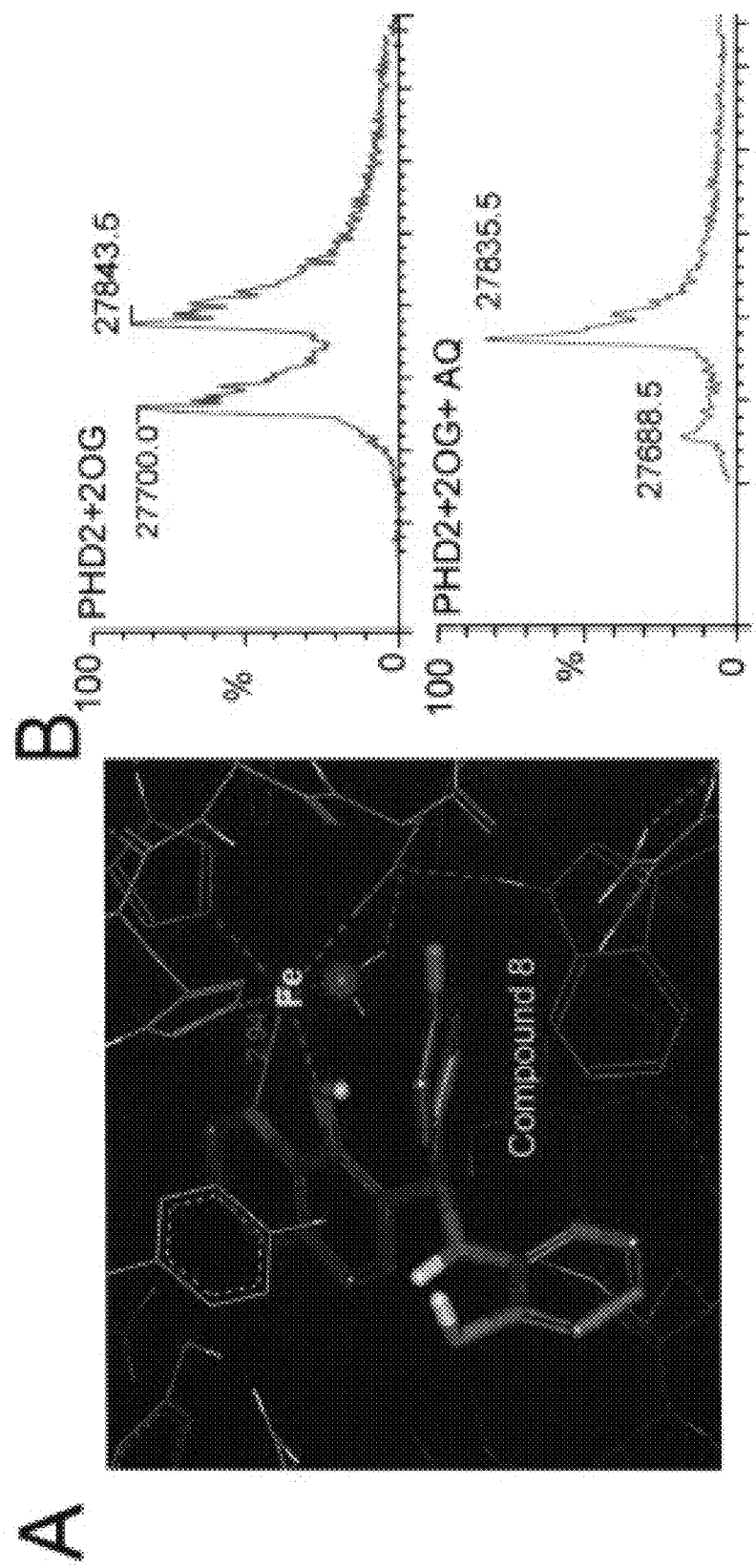
FIGS. 3A-3G. Validation of adaptoquin as a novel HIF PHD inhibitor.
Figure 3C:
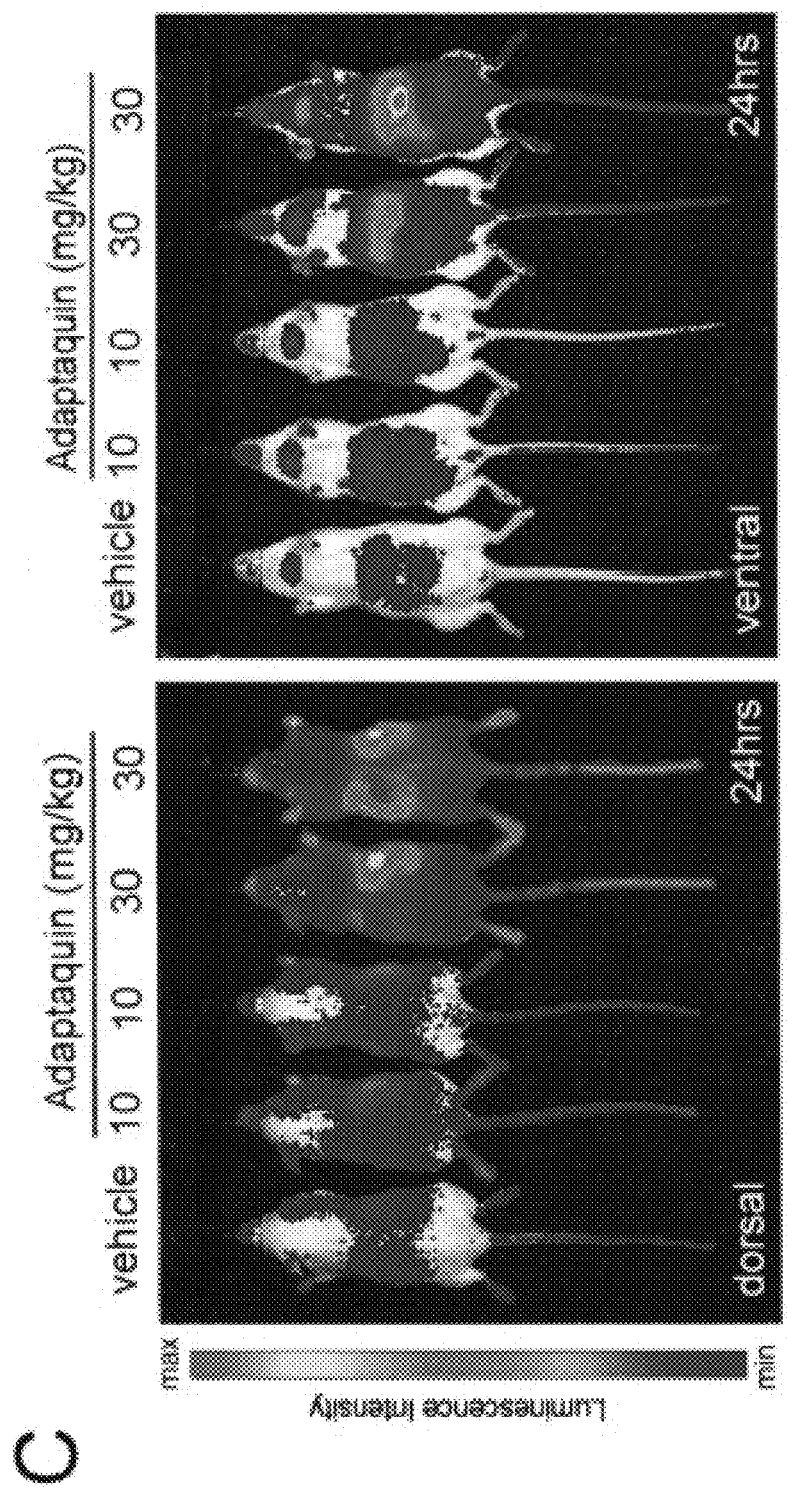
Figures 3D, 3E, 3F, 3G:
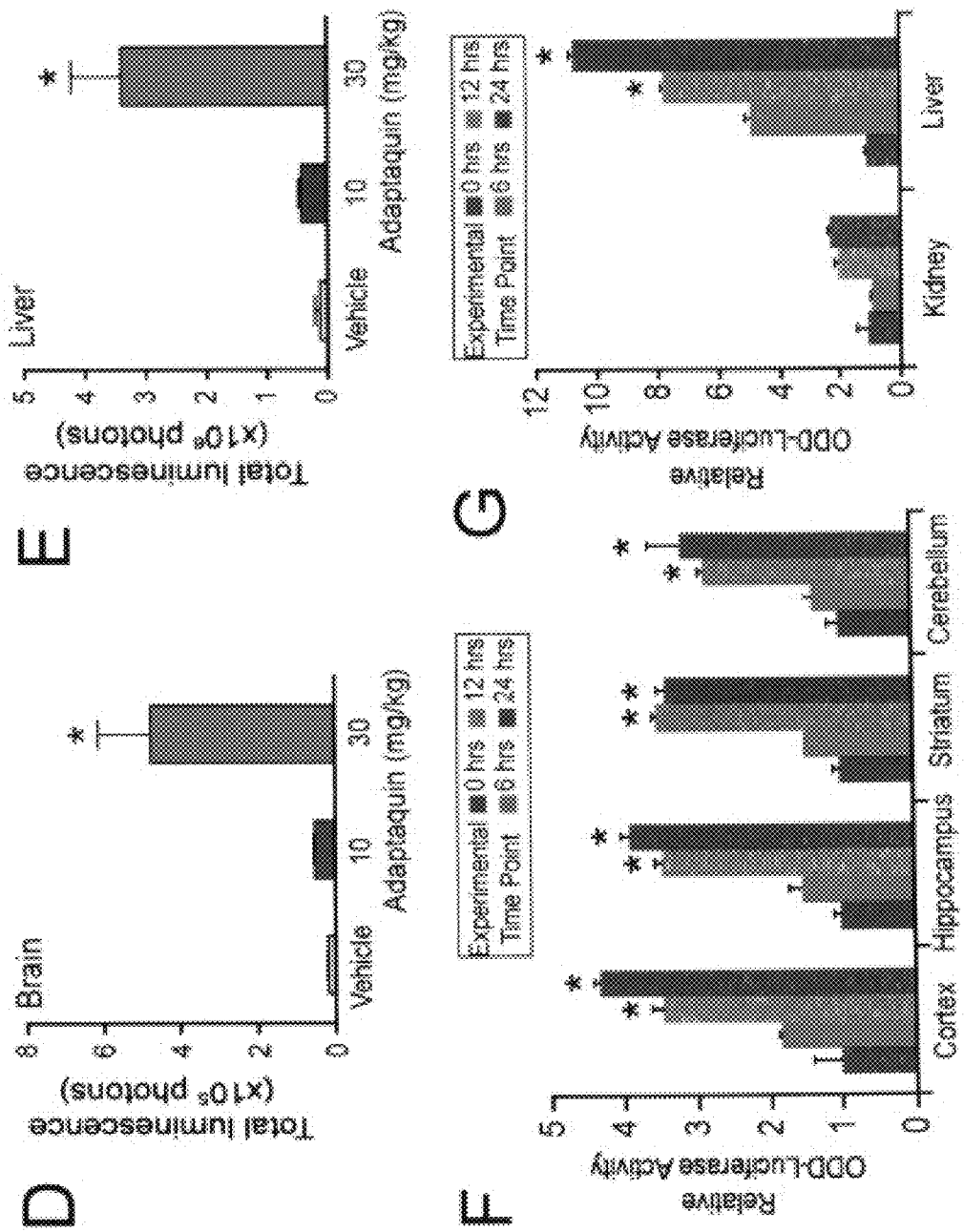
Figures 4A, 4B, 4C, 4D:
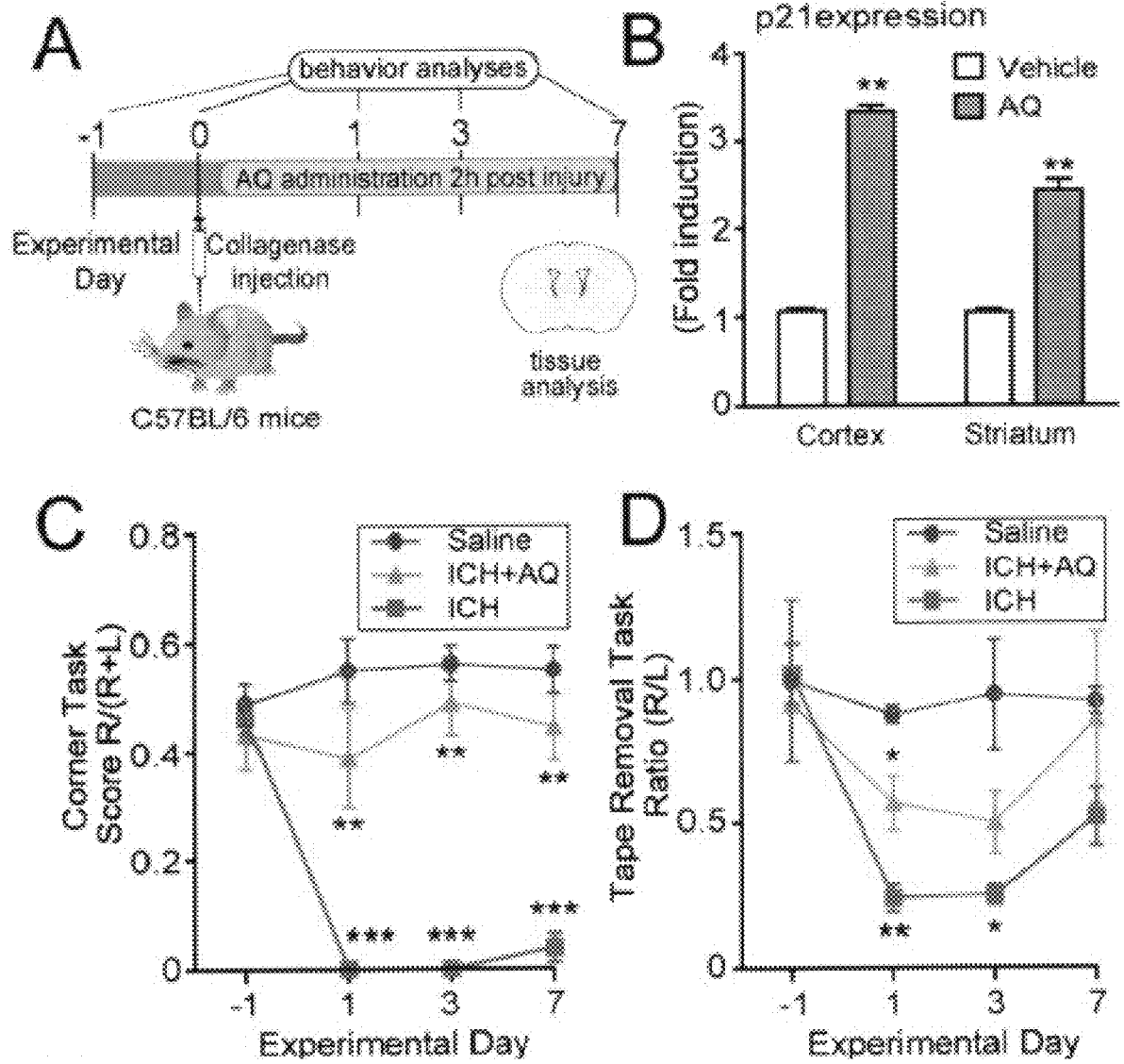
Figures 4E, 4F, 4G:
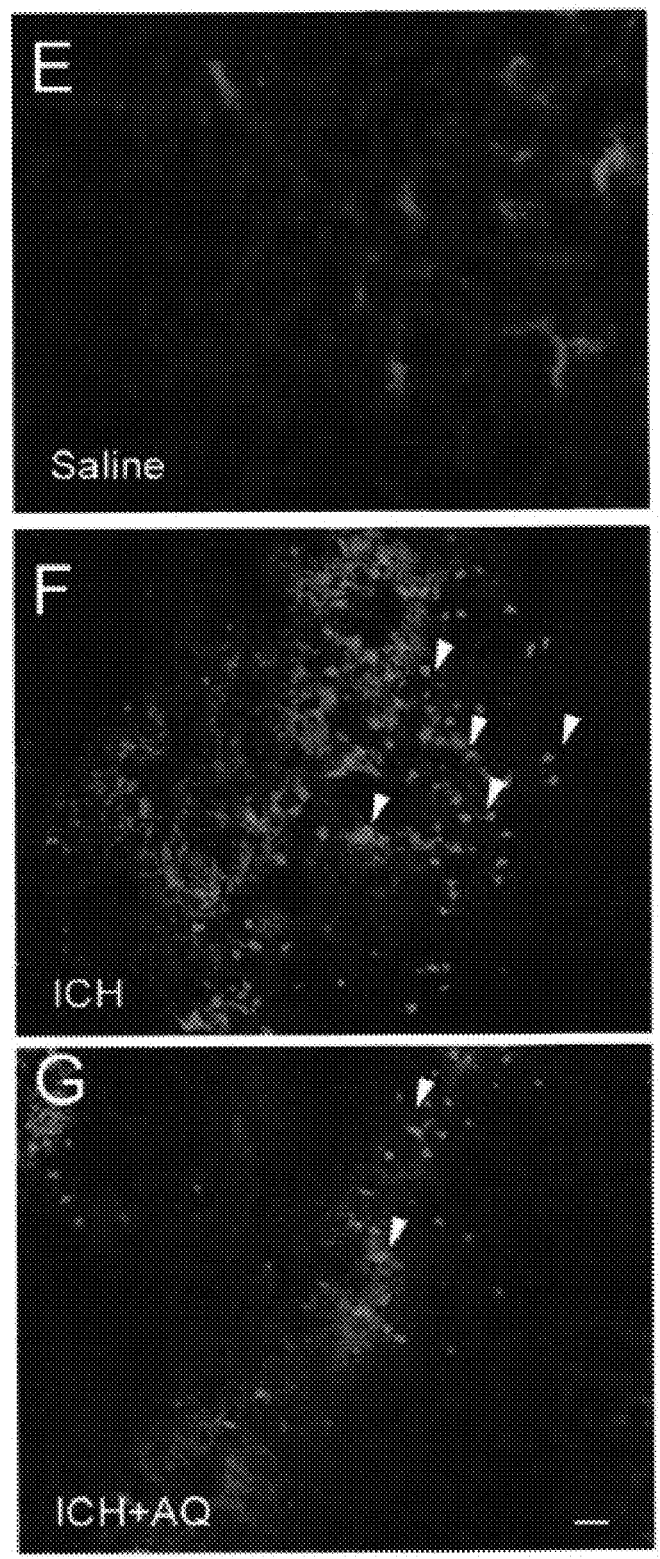
Figures 4H, 4I:
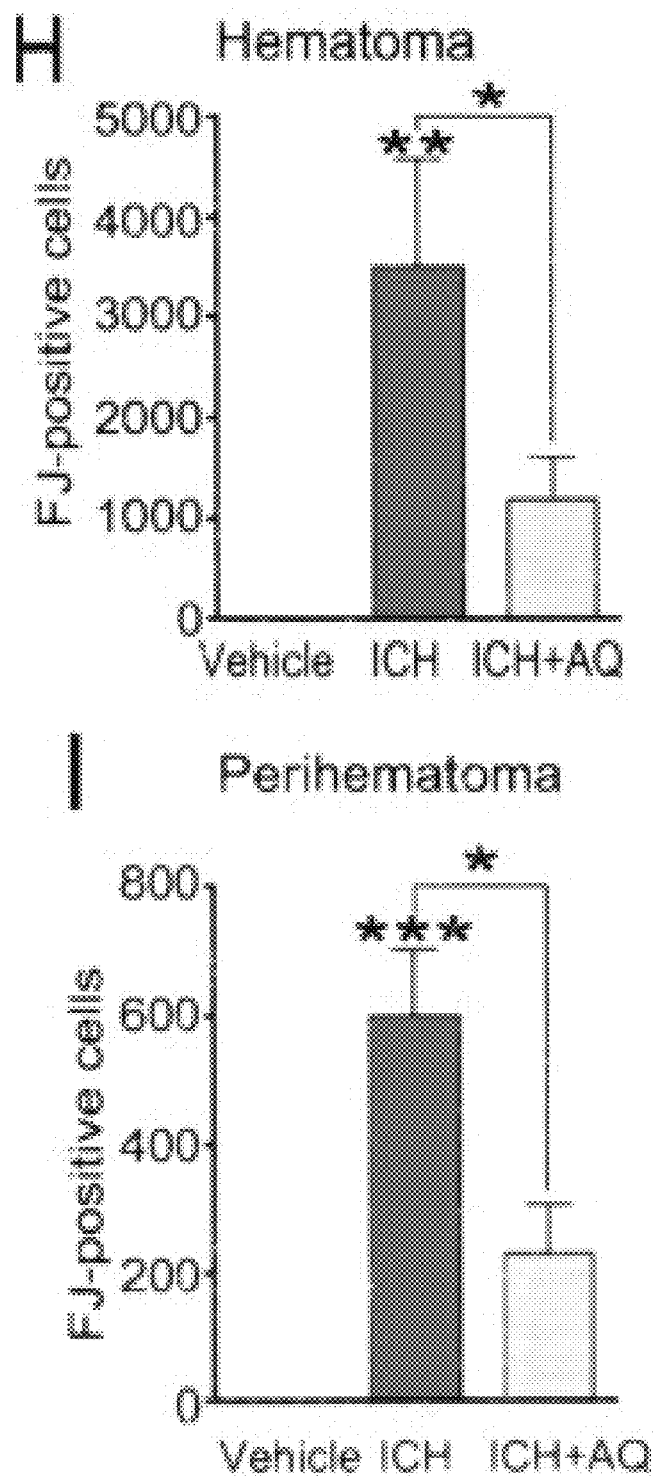
FIGS. 4H, 4I: Apatoquin significantly reduces neuronal degeneration as monitored by Fluoro-jade staining.
Figure 4J:
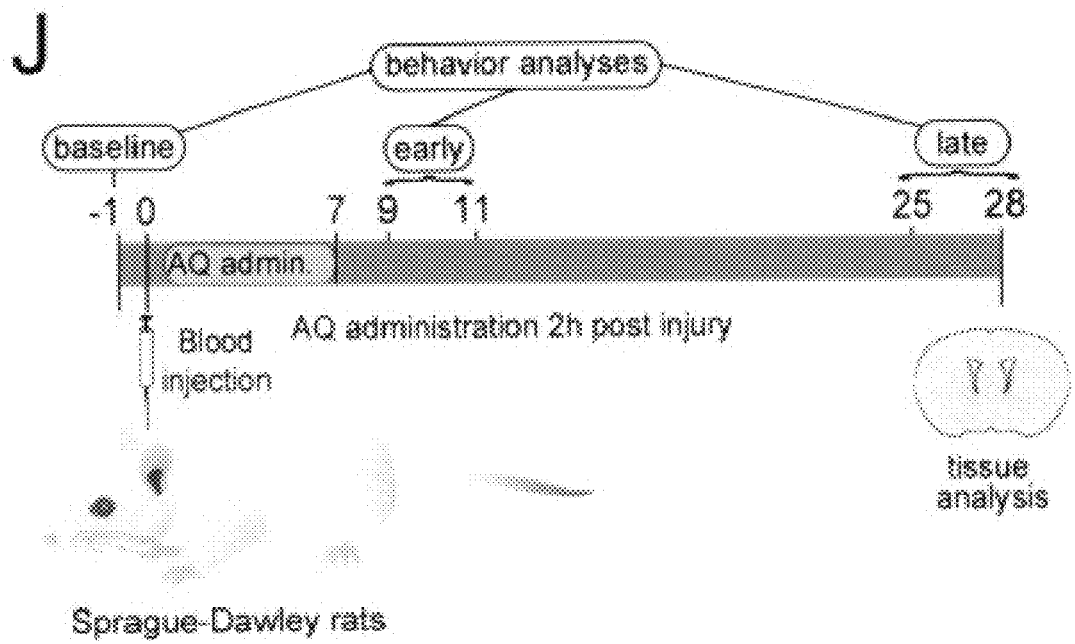
FIG. 4J: Protocol for adaptoquin treatment of rats with ICH. ICH is modeled by autologous blood infusion and not collagenase in these studies. Behavior is tracked by a single pellet reaching task out to 28 days, but the schedule of infusion is similar to what is used in mice-2 hrs post blood infusion and then daily out to seven days. Behavior is monitored before, from 9-11 days and from 25-28 days.
Figure 4K:
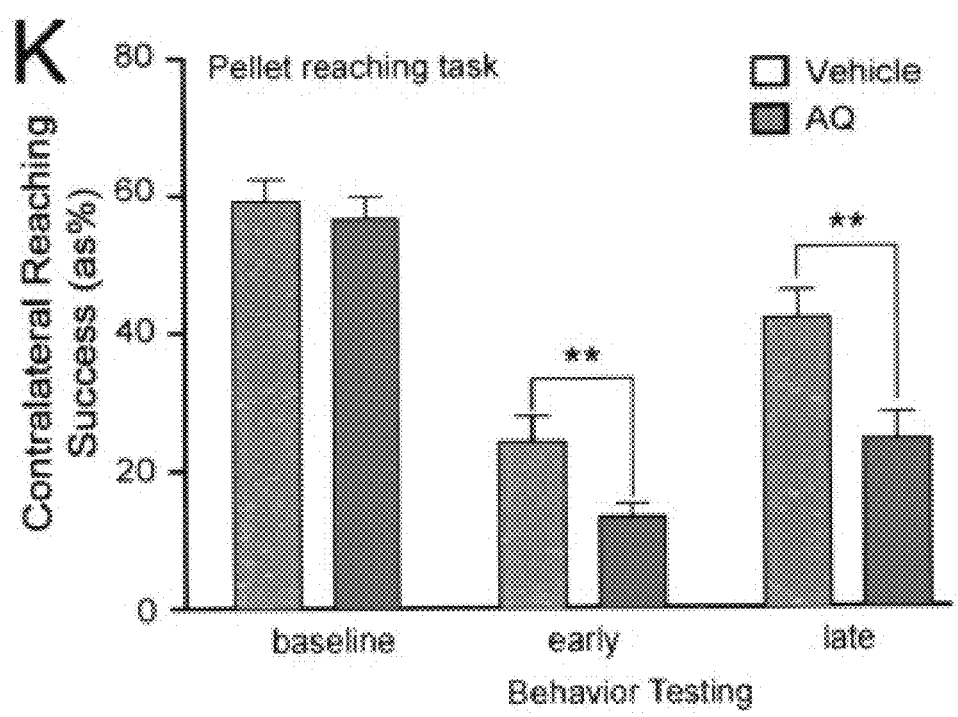
FIG. 4K: Adaptoquin improves single pellet reaching in rats following ICH out to 28 days.
Figures 4L, 4M, 4N:
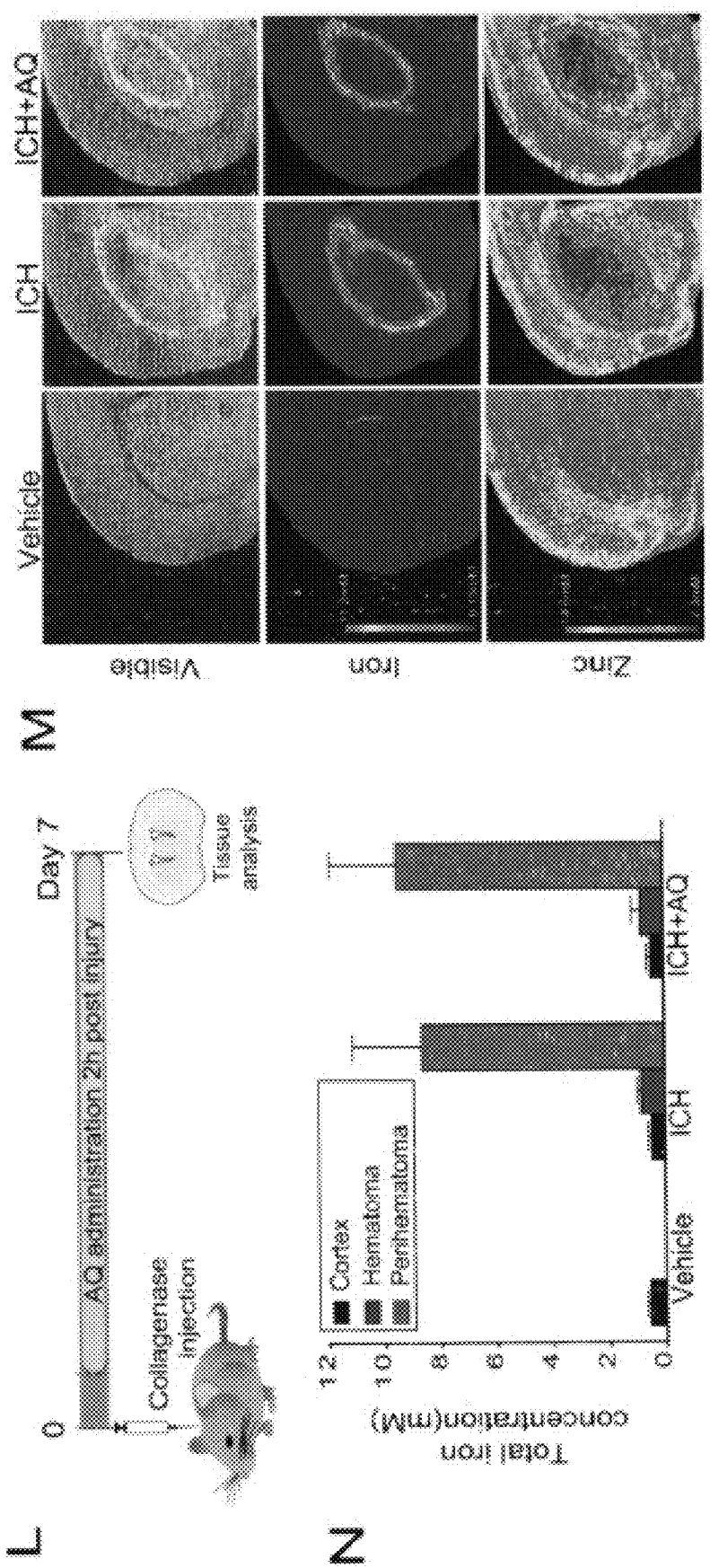
Figure 5A:
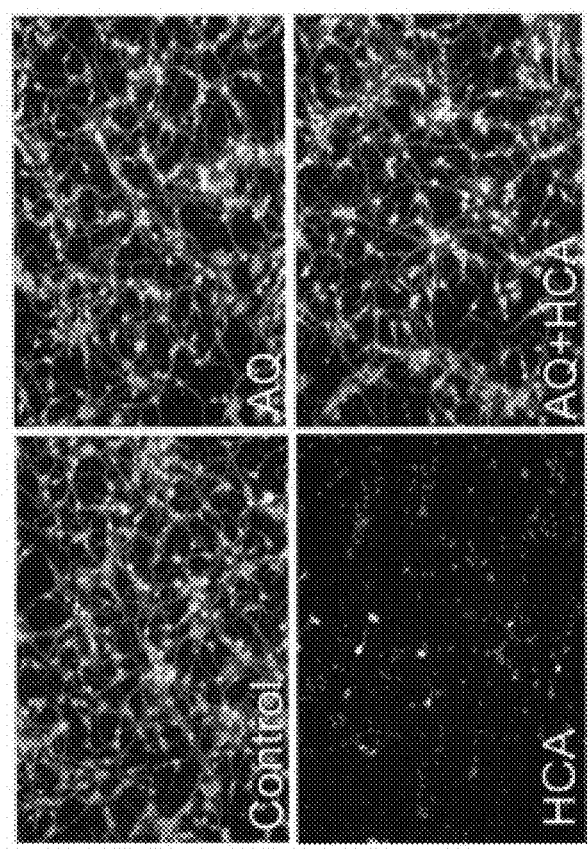
FIGS. 5A-5G. Adaptoquin prevents hemin induced death independent of HIF-1 and HIF-2 that is significantly associated with ATF4 dependent gene expression. Because adaptoquin is a HIF PHD inhibitor that appears to work independent of HIF transcription factors, and because hemin induced death involves oxidative stress, the effect of adaptoquin on oxidative glutamate toxicity was examined. This form of toxicity is observed in primary cortical neurons from E17 rat embryos (2 DIV) and involves glutamate mediated inhibition of the amino acid cystine via its plasma membrane transporter. Hemin induced toxicity and glutamate induced toxicity both can be abrogated by GPX4, suggesting that they share common mechanisms. Accordingly, the optimal concentration of adaptoquin in protecting neurons was first determined and found to be about 1 micromolar.
Figure 5B:
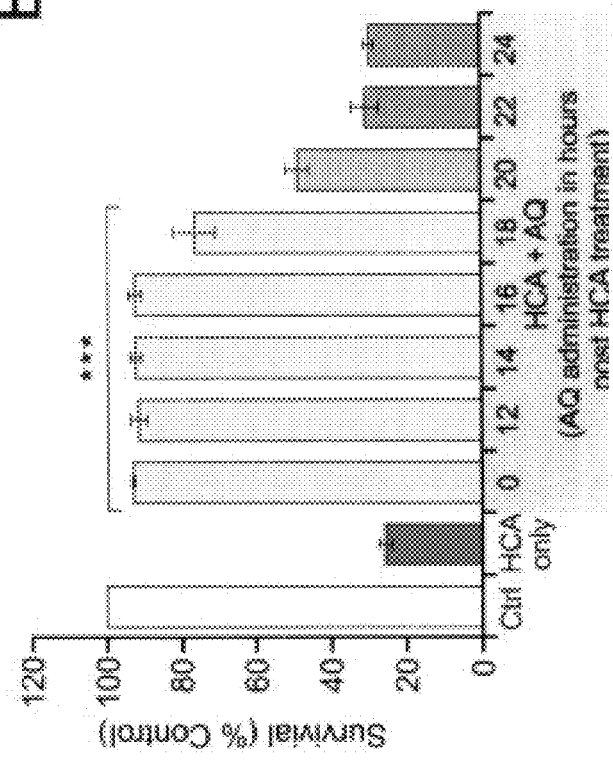
Figure 5C:
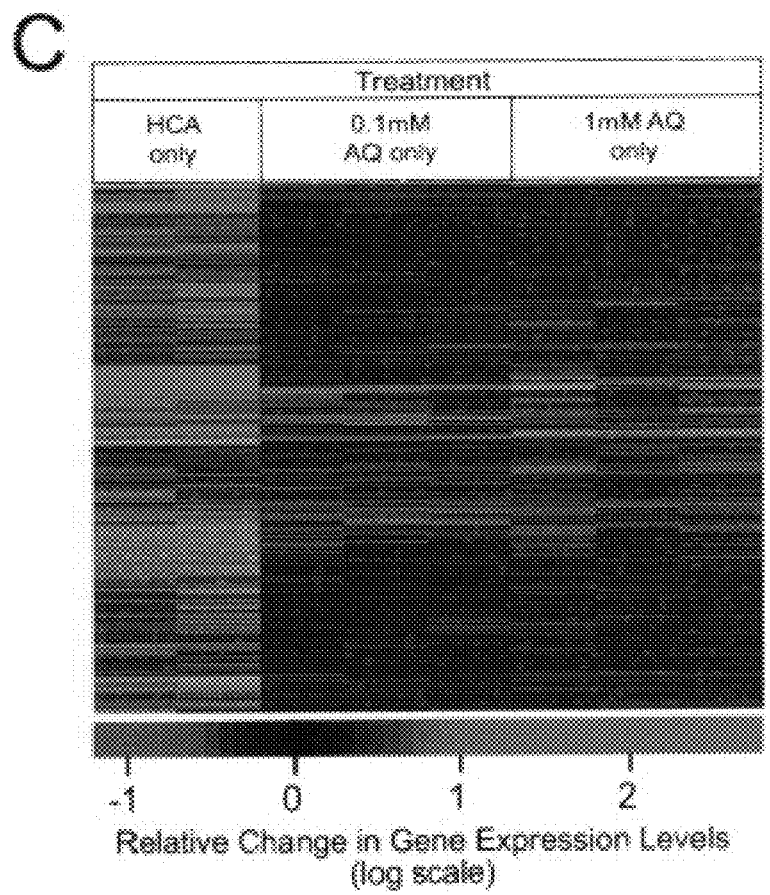
Figure 5D:
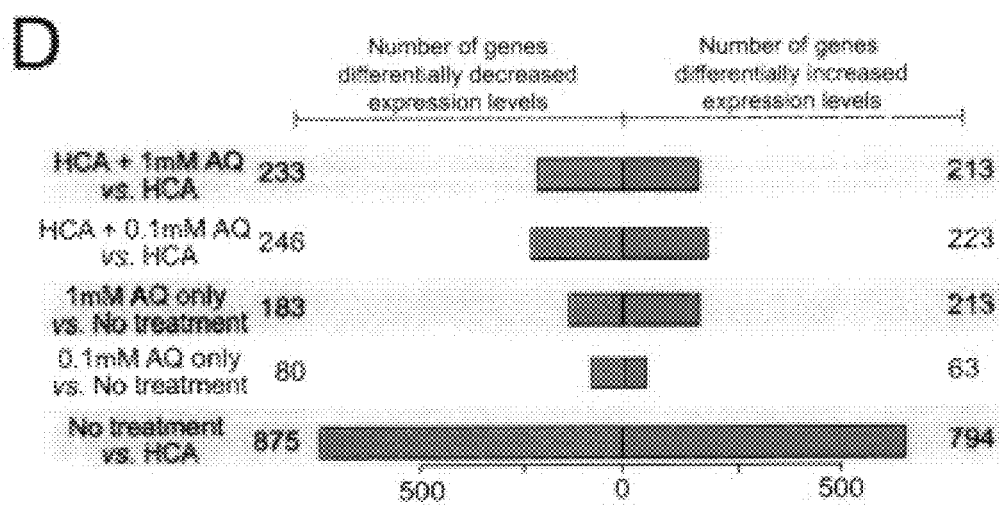
Figure 5E:
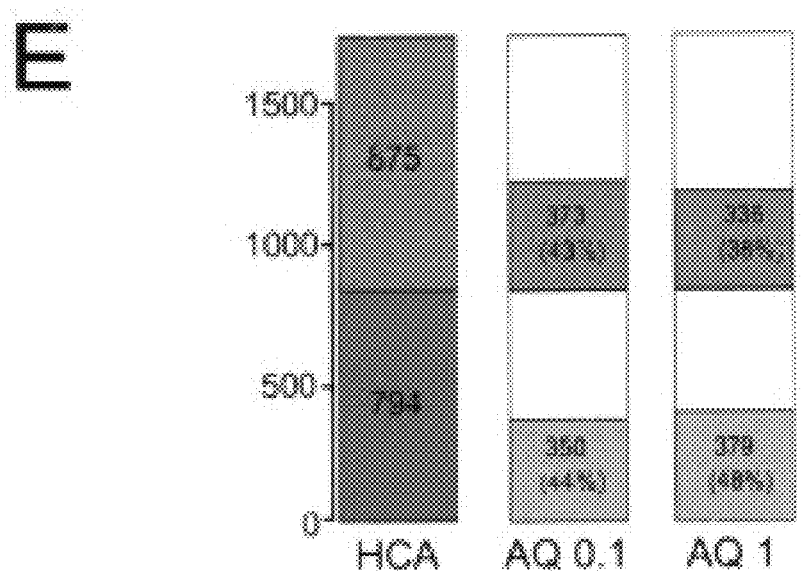
Figure 5F:
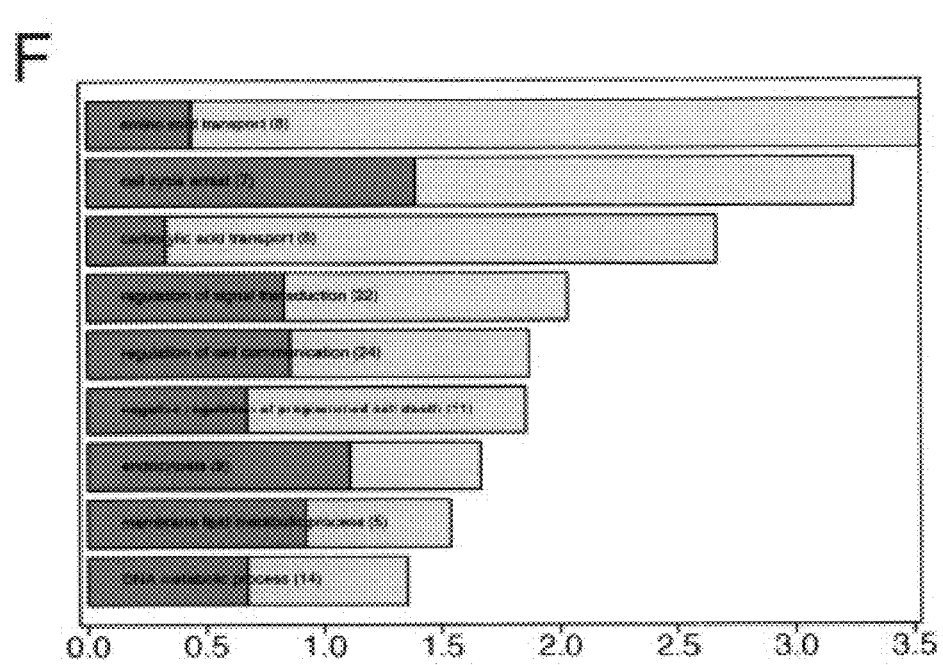
Figure 5G:
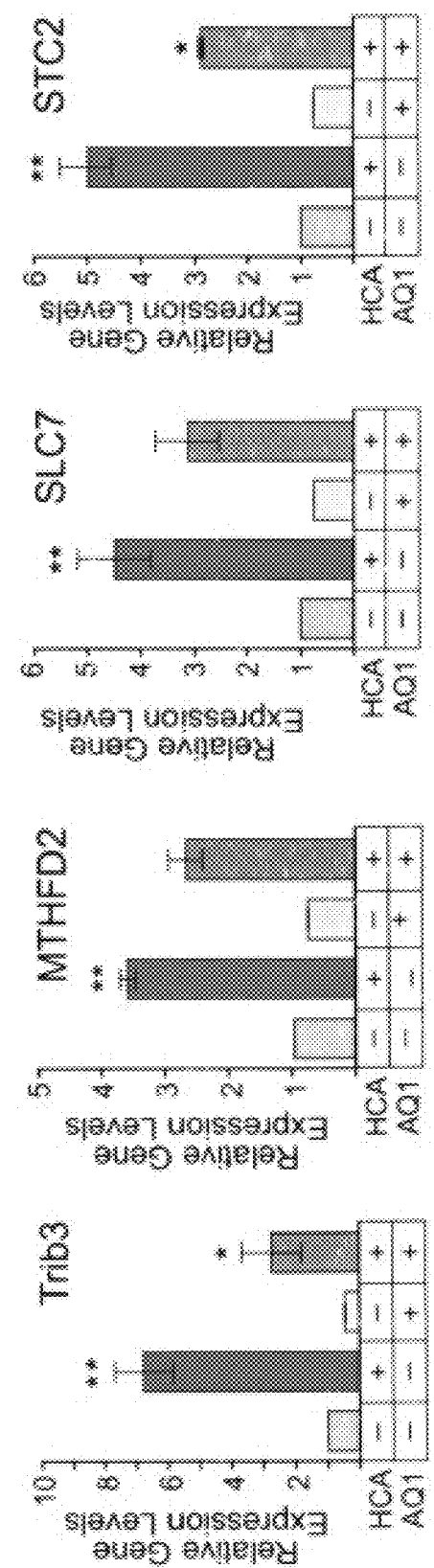
Figures 6A, 6B:
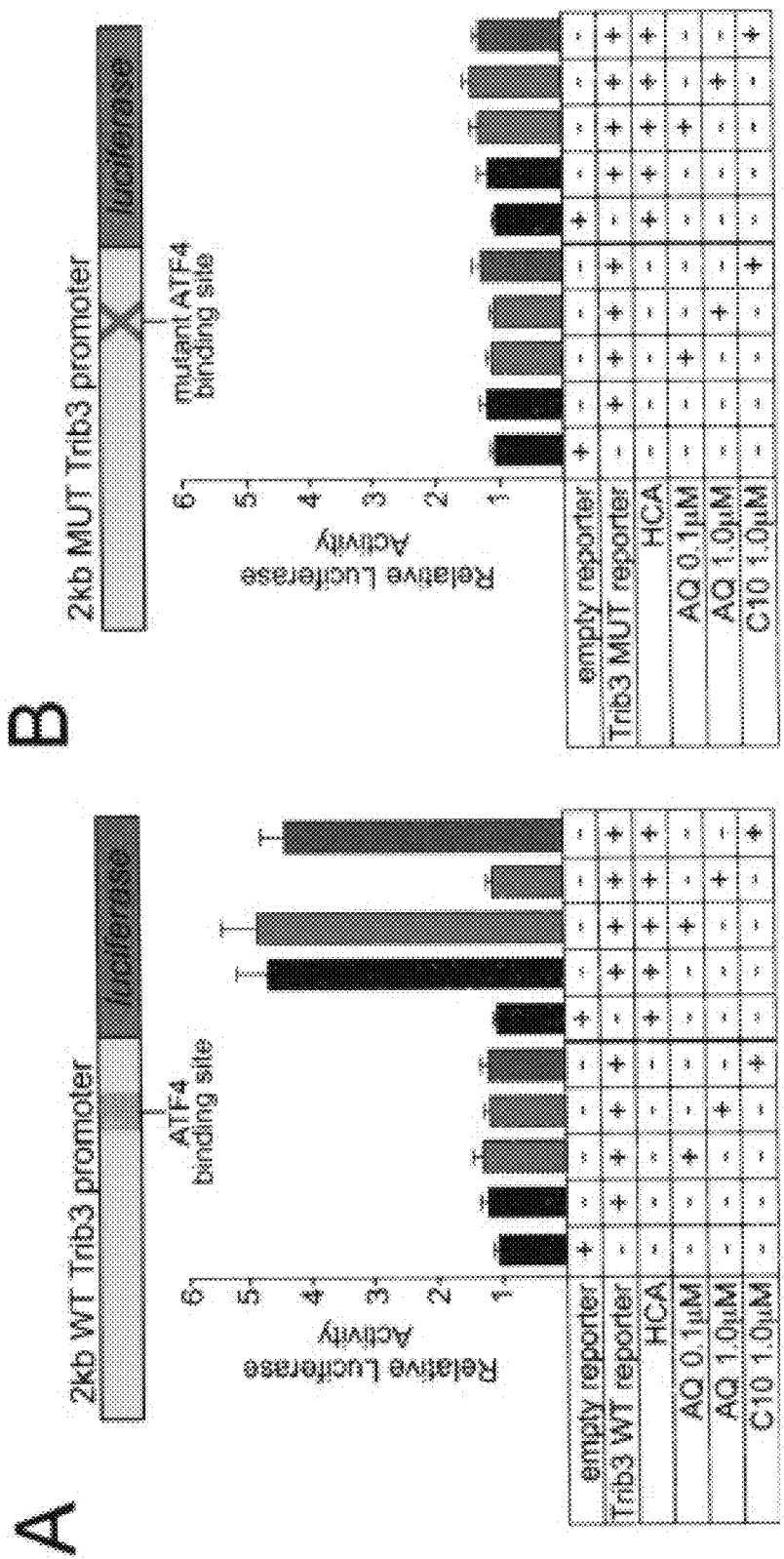
FIGS. 6A-6I. Protective concentrations of adaptoquin (1 micromolar) but not non-protective concentrations (0.1 micromolar) or an inactive analog (FIG. 6C, 1 micromolar) abrogates oxidative stress and ATF4 dependent induction of Trb3, a death associated gene.
Figure 6C:
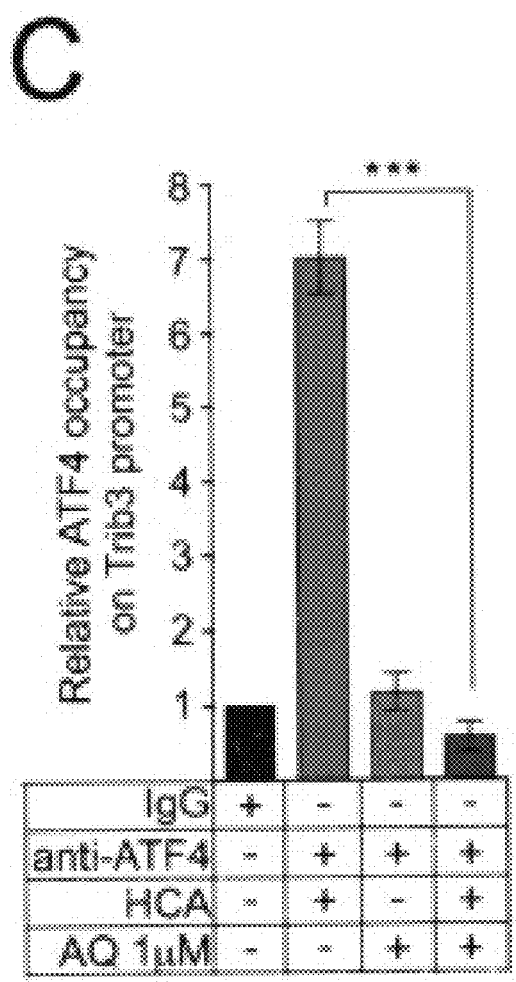
Figure 6D:
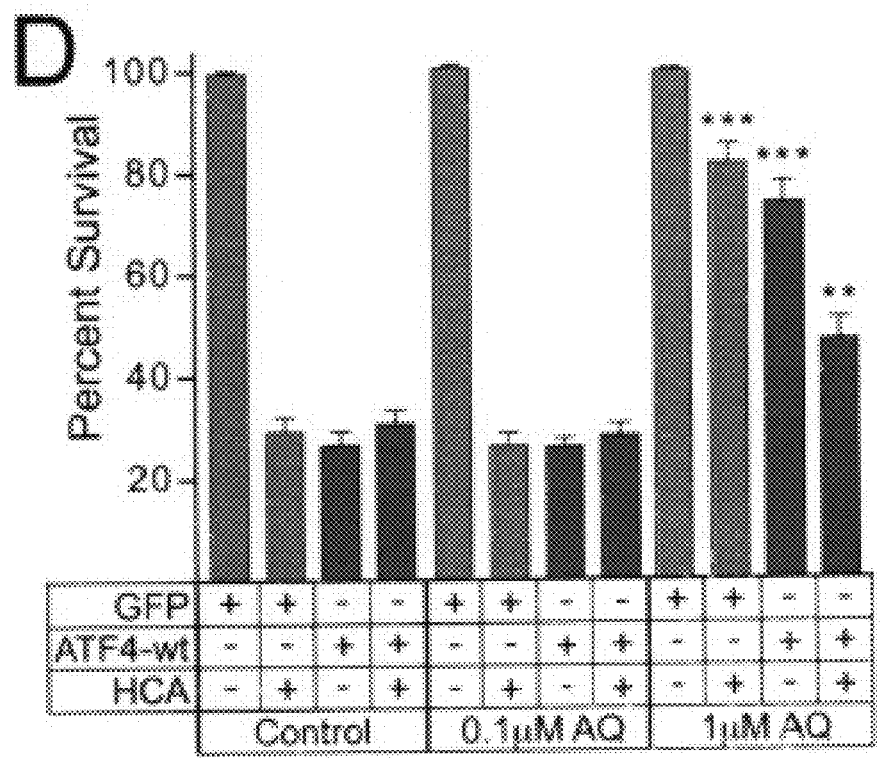
Figure 6E:
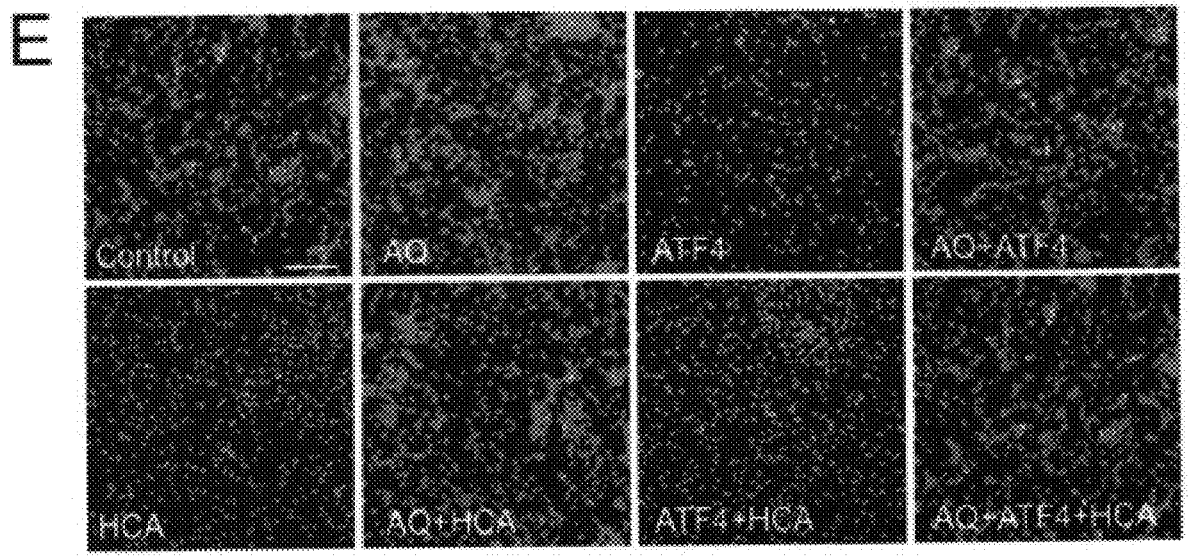
Figures 6F, 6G, 6H, 6I:
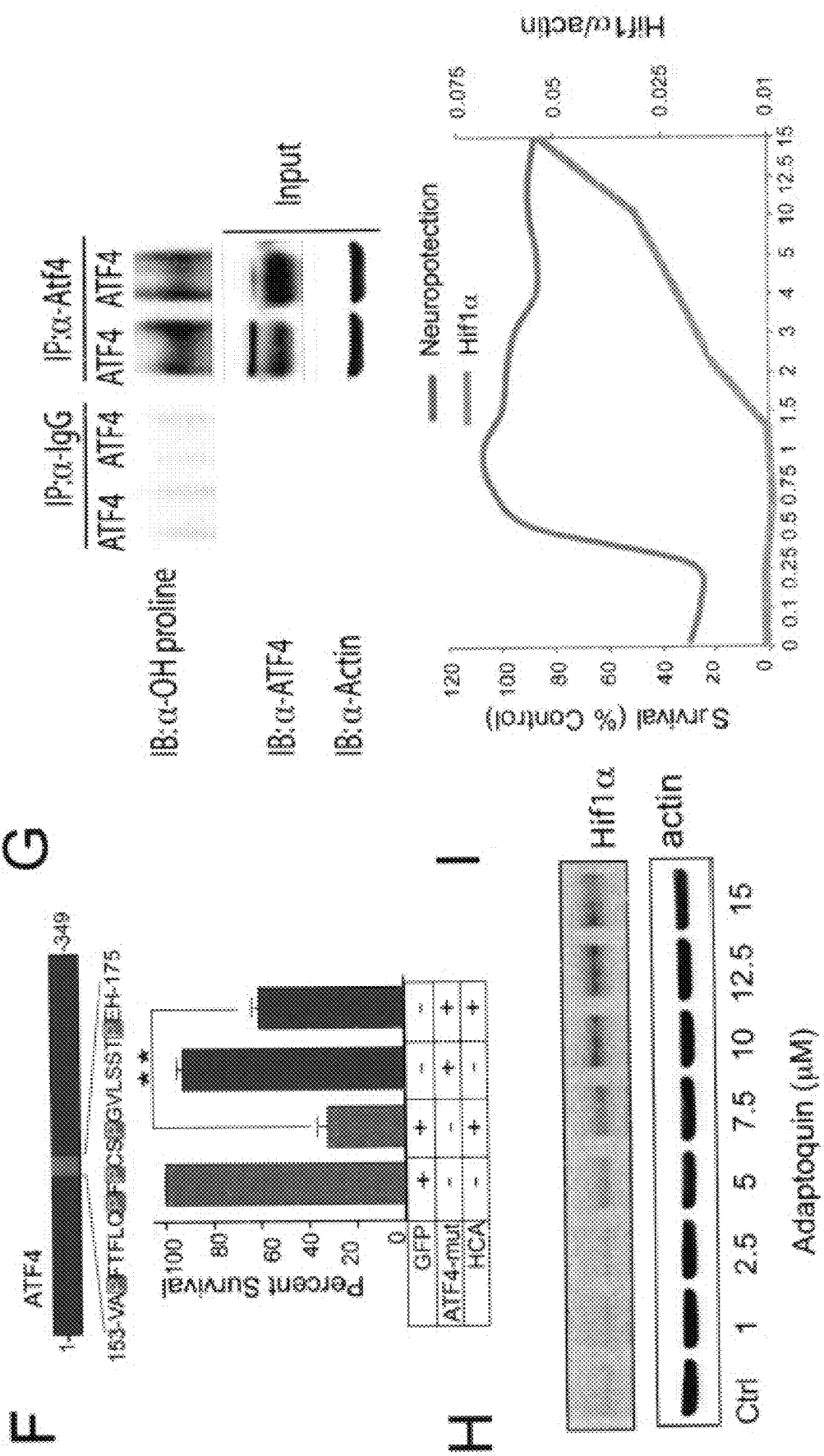

For convenience, before further description of the present invention, certain terms employed in the specification, examples, and appended claims are described here. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing.

A "fusion protein" or "fusion polypeptide" refers to a chimeric protein as that term is known in the art. A fusion protein or polypeptide may be synthesized by methods known in the art. In many examples of fusion proteins, there are two different polypeptide sequences, and in certain cases, there may be more. The sequences may be linked in frame. A fusion protein may include a domain found (albeit in a different protein) in an organism that also expresses the first protein, or it may be an "interspecies", "intergenic", or related fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a green fluorescent protein tag (GFP-tag), glutathione S transferase tag (GST-tag), histidine tag (His-tag), an immunoglobulin domain or an immunoglobulin binding domain.

The term "motif" generally refers to an amino acid sequence within a protein that has a particular function in the enzymatic process. The function can involve, for example, binding of a substrate, binding of a cofactor, or participation in catalysis.

"Target genes" of a transcription factor are native cellular genomic sequences whose transcriptional expression is controlled by the transcription factor.

A "transcription factor" is a protein that, through binding to a cellular genomic DNA sequence or by facilitating the interaction of other proteins to such sequence, allows synthesis of mRNA, "transcription", from such genomic DNA sequence.

As used herein, the term "hydrocarbon group" (also denoted by the group R) is, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a number of carbon atoms within a particular range bounded by any two of the foregoing carbon numbers. Hydrocarbon groups or linkers in different compounds described herein, or in different positions of a compound, may possess the same or different number (or preferred range thereof) of carbon atoms in order to independently adjust or optimize the activity or other characteristics of the compound. The term "hydrocarbon linker", as used herein, is a linking group that may be derived by any of the hydrocarbon groups by including at least one additional linking point by removal of one or more hydrogen atoms from the group (e.g., a —CH$_2$CH$_2$— or >CHCH$_3$ linking group can be derived from an ethyl (—CH$_2$CH$_3$) group by removal of one of the hydrogen atoms of the ethyl group, either from an adjacent carbon atom or same carbon atom, respectively).

The hydrocarbon groups or linkers (R) can be, for example, saturated and straight-chained (i.e., straight-chained alkyl groups or alkylene linkers). Some examples of straight-chained alkyl groups (or alkylene linkers) include methyl (or methylene linker, i.e., —CH$_2$—, or methine linker), ethyl (or ethylene or dimethylene linker, i.e., —CH$_2$CH$_2$— linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers (R) can alternatively be saturated and branched (i.e., branched alkyl groups or alkylene linkers). Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 carbon atoms, wherein the "1-yl" suffix represents the point of attachment of the group. Some examples of branched alkylene linkers are those derived by removal of a hydrogen atom from one of the foregoing exemplary branched alkyl groups (e.g., isopropylene, —CH(CH$_3$)CH$_2$—).

The hydrocarbon groups or linkers (R) can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers (R) can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2=CH-CH_2-CH_2-$), 2-buten-1-yl ($CH_2-CH=CH-CH_2-$), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous other straight-chained alkenyl groups having up to 20 carbon atoms. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers (R) can alternatively be unsaturated and branched (i.e., branched olefinic or alkenyl groups or linkers). Some examples of branched olefinic groups include propen-2-yl ($CH_2=C.-CH_3$), 1-buten-2-yl ($CH_2=C.-CH_2-CH_3$), 1-buten-3-yl ($CH_2=CH-CH.-CH_3$), 1-propen-2-methyl-3-yl ($CH_2=C(CH_3)-CH_2-$), 1-penten-4-yl, 1-penten-3-yl, 1-penten-2-yl, 2-penten-2-yl, 2-penten-3-yl, 2-penten-4-yl, and 1,4-pentadien-3-yl, wherein the dot in any of the foregoing groups indicates a point of attachment. Some examples of branched olefinic linkers are those derived by removal of a hydrogen atom from one of the foregoing exemplary branched olefinic groups.

The hydrocarbon groups or linkers (R) can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers (R) may (i.e., optionally) include one or more heteroatoms, which are non-carbon non-hydrogen atoms. Some examples of heteroatoms include oxygen (O), nitrogen (N), sulfur (S), and halogen (halide) atoms. Some examples of halogen atoms include fluorine, chlorine, bromine, and iodine.

In the case of heteroatom-containing linkers, the linker may contain one or more heteroatoms. In the case of a single heteroatom, the heteroatom may itself serve as a linker by inserting between at least two carbon atoms, i.e., as a —O—, —NR'—, or —S— linker (as in —C—O—C— ether, —C—S—C— thioether, —C—N(R')—C— tertiary amine, or —C=N—C— imine linkages), wherein the shown carbon atom in each case can be considered part of a hydrocarbon group R described above, and R' independently represents hydrogen atom or any of the hydrocarbon groups (R) described above. Alternatively, the linker may contain one or more heteroatoms attached to a carbon atom, wherein the carbon atom of the linker links between two carbon atoms, e.g., a carbonyl (—C(O)—), thiocarbonyl (—C(S)—), or dihalomethylene (—$CX_2$—) linker, where X represents a halogen atom. The heteroatom-containing linker may alternatively contain two or more heteroatoms, as in ester (—C(O)O—), thioester (—C(S)O—), carboxamide (—C(O)NR'—), thiocarboxamide (—C(S)NR'—), urea (—NR'—C(O)—NR'—), thiourea (—NR'—C(S)—NR'—), carbamate (—NR'—C(O)—O—), thiocarbamate (—NR'—C(S)—O—), azo (—N=N—), sulfonyl (—$S(O)_2$—), sulfinyl (—S(O)—), and disulfide (—S—S—) linkers.

A heteroatom-containing group may be derived by replacing one or more hydrogen and/or carbon atoms or C—H or $CH_2$ groups in a hydrocarbon group (R) with one or more heteroatoms, and/or by inserting one or more heteroatoms between carbon atoms of the hydrocarbon group (R). Some examples of heteroatom-containing groups include halogen-substituted groups (e.g., —$CH_2F$, —$CHF_2$, and —$CF_3$), carbonyl-containing groups (e.g., —C(O)R', which includes ketone and aldehyde groups), amino groups (—$NR'_2$), hydroxy and alkoxy groups (—OR'), carboxy-containing groups (—C(O)OR' or —OC(O)R'), thiocarboxy-containing groups (—C(S)OR' or —OC(S)R'), carboxamide-containing groups (—$C(O)NR'_2$ or —N(R')C(O)R'), urea-containing groups (—NR'—C(O)—$NR'_2$), thiourea-containing groups (—NR'—C(S)—$NR'_2$), carbamate-containing groups (—NR'—C(O)—OR' or —OC(O)—$NR'_2$), thiocarbamate-containing groups (—NR'—C(S)—OR' or —OC(S)—$NR'_2$), nitrile (CN), sulfonyl-containing groups (—$S(O)_2R'$), sulfinyl-containing groups (—S(O)R'), and amine oxide (as typically found in a nitrogen-containing ring), wherein R' independently represents hydrogen atom or any of the hydrocarbon groups (R) described above. For example, —C(O)OR' includes carboxylic acid (—C(O)OH) and carboxylic ester (—C(O)OR), and —OR' includes hydroxy (OH) and alkoxy (OR), where R is selected from any of the hydrocarbon groups described above. Other heteroatom-containing groups made only of heteroatoms (e.g., nitro, i.e., $NO_2$) are also considered.

In some embodiments, the hydrocarbon group or linker is substituted with multiple oxygen atoms to result in a dialkyleneoxide or polyalkyleneoxide group, such as a diethyleneoxide or polyethyleneoxide group. The polyalkylene oxide group may, for example, be of the formula —($CH_2CR'_2O)_n$—, where R' is a hydrogen atom or hydrocarbon group, as described above, but more typically independently selected from hydrogen and methyl groups.

In the case of nitrogen or sulfur substitution, the nitrogen or sulfur atom may be bound to a sufficient number of groups to make it positively charged, as in an ammonium group (e.g., —$NR'_3{}^+$) or sulfonium group (e.g., —$SR'_2{}^+$), in which case the positively charged moiety is necessarily associated with a counteranion (wherein R' independently represents hydrogen atom or any of the hydrocarbon groups described above). Likewise, a heteroatom may bear a negative charge, as in a deprotonated carboxy, thiocarboxy, sulfonate, phosphonate, hydroxy, or thiol group, in which case the negatively charged moiety is necessarily associated with a countercation.

In particular embodiments, the hydrocarbon group is, or includes, a cyclic group that contains at least three and up to seven ring carbon atoms. The cyclic group may be, for example, monocyclic by containing a single ring without connection or fusion to another ring. The cyclic group may alternatively be, for example, bicyclic, tricyclic, tetracyclic, or a higher polycyclic ring system by having at least two rings interconnected and/or fused.

In some embodiments, the cyclic group is carbocyclic, i.e., does not contain ring heteroatoms (i.e., only ring carbon atoms). In different embodiments, the carbocyclic group is completely saturated, or a portion of the carbocyclic group is unsaturated, or the carbocyclic group is completely unsaturated, e.g., an aromatic carbocyclic group, which may be a monocyclic, bicyclic, tricylic, or higher polycyclic aromatic group. Numerous examples of saturated and unsaturated carbocyclic rings have been provided above.

In some embodiments, the cyclic group is a monocyclic or polycyclic group that includes at least one ring heteroatom, e.g., one, two, three, four, or higher number of heteroatoms. Such ring heteroatom-substituted cyclic groups are referred to herein as "heterocyclic groups" or "heterocyclic rings". As used herein, a "ring heteroatom" is an atom other than carbon and hydrogen (typically, selected from nitrogen, oxygen, and sulfur) that is inserted between ring carbon atoms or that replaces a ring carbon atom in a carbocyclic ring. In some embodiments, the heterocyclic ring is saturated, while in other embodiments the heterocyclic ring is unsaturated, wherein the unsaturated heterocyclic ring may be aliphatic or aromatic. An aromatic heterocyclic ring is also referred to herein as a "heteroaromatic ring", or a "heteroaromatic fused-ring system" in the case of at least two fused rings, at least one of which contains at least one ring heteroatom.

In one set of embodiments, the heterocyclic ring (which may be a monocyclic ring or polycyclic ring system) is saturated. Some examples of saturated heterocyclic rings containing at least one oxygen atom include oxetane, tetrahydrofuran, tetrahydropyran, 1,4-dioxane, 1,3-dioxane, and 1,3-dioxepane rings. Some examples of saturated heterocyclic rings containing at least one nitrogen atom include pyrrolidine, piperidine, piperazine, imidazolidine, azepane, and decahydroquinoline rings. Some examples of saturated heterocyclic rings containing at least one sulfur atom include tetrahydrothiophene, tetrahydrothiopyran, 1,4-dithiane, 1,3-dithiane, and 1,3-dithiolane rings. Some examples of saturated heterocyclic rings containing at least one oxygen atom and at least one nitrogen atom include morpholine and oxazolidine rings. An example of a saturated heterocyclic ring containing at least one oxygen atom and at least one sulfur atom includes 1,4-thioxane. Some examples of saturated heterocyclic rings containing at least one nitrogen atom and at least one sulfur atom includes thiazolidine and thiamorpholine rings.

In another set of embodiments, the heterocyclic ring (which may be a monocyclic ring or polycyclic ring system) is unsaturated. Some examples of unsaturated heterocyclic rings containing at least one oxygen atom include furan, pyran, 1,4-dioxin, 1,2-benzodioxane, 1,3-benzodioxane, 1,4-benzodioxane, 1,3-benzodioxole, and dibenzodioxin rings. Some examples of unsaturated heterocyclic rings containing at least one nitrogen atom include pyrrole, imidazole, pyrazole, pyridine, pyrazine, pyrimidine, 1,3,5-thazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings. Some examples of unsaturated heterocyclic rings containing at least one sulfur atom include thiophene, thianaphthene, and benzothiophene rings. Some examples of unsaturated heterocyclic rings containing at least one oxygen atom and at least one nitrogen atom include oxazole, isoxazole, benzoxazole, benzisoxazole, oxazoline, 1,2,5-oxadiazole (furazan), and 1,3,4-oxadiazole rings. Some examples of unsaturated heterocyclic rings containing at least one nitrogen atom and at least one sulfur atom include thiazole, isothiazole, benzothiazole, benzoisothiazole, thiazoline, and 1,3,4-thiadiazole rings.

The method described herein in the treatment of neural cell injury or death employs a compound having the following chemical structure:

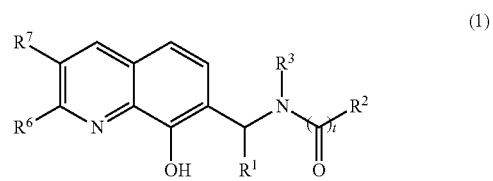

(1)

In Formula (1), the subscript t in formula (1) is a number of 0 or 1. When t is 0, the subtended carbonyl group is not present, thereby resulting in an amino group in which the shown nitrogen atom (attached to $R^3$) is directly bound to $R^2$. When t is 1, the subtended carbonyl group is present, thereby resulting in an amido group.

The group $R^1$ is a cyclic group, as described above, that contains at least three and up to seven ring carbon atoms and optionally contains one or more ring heteroatoms selected from O, N, and S. Thus, the group $R^1$ can be any of the saturated or unsaturated, and carbocyclic or heterocyclic, and monocyclic or polycyclic groups described above. In particular embodiments, the cyclic group of $R^1$ is selected from five- or six-membered saturated or unsaturated rings that may be heteroatom-unsubstituted or heteroatom-substituted with one or two heteroatoms selected from nitrogen, oxygen, and sulfur. Some particular examples of $R^1$ include cyclohexyl, cyclohexenyl, cyclohexadienyl, cyclopentyl, cyclopentenyl, cyclopentadienyl, phenyl, piperidinyl, piperazinyl, pyridinyl, pyrazinyl, pyrrolidinyl, imidazolyl, indolyl, benzimidazolyl, quinolinyl, isoquinolinyl, phenanthrolinyl, furyl, pyranyl, dioxinyl, benzodioxinyl, and 1,3-benzodioxolyl rings.

In some embodiments, the cyclic group of $R^1$ contains ring hydrogen atoms that are all unsubstituted, i.e., ring hydrogen atoms not replaced with a substituting group. The ring hydrogen atoms refer to hydrogen atoms on ring carbon atoms as well as on ring heteroatoms. Such a cyclic group is herein referred to as an "unsubstituted cyclic group". In other embodiments, the cyclic group of $R^1$ is substituted by having at least one ring hydrogen atom that has been substituted with a substituting (i.e., non-hydrogen atom) group selected from —$R^4$, —C(O)$R^4$, —N$R^4_2$, —O$R^4$, —NO$_2$, —C(O)N$R^4_2$, —N$R^4$C(O)$R^4$, —C(O)O$R^4$, —OC(O)$R^4$, —OC(O)N$R^4_2$, —N$R^4$C(O)N$R^4_2$, —N$R^4$C(O)O$R^4$, —SO$_2R^4$, nitrile, and halogen atom, wherein $R^4$ is, independently, a hydrogen atom or an acyclic hydrocarbon group containing up to six carbon atoms (i.e., one, two, three, four, five, or six carbon atoms or a number of carbon atoms within a range therein). Thus, the cyclic group of $R^1$ may have one, two, or more substituting groups $R^4$. The hydrocarbon group $R^4$ may be saturated or unsaturated, straight-chained or branched, cyclic or acyclic, and may be heteroatom-unsubstituted or heteroatom-substituted. Some particular examples of $R^4$ include methyl, ethyl, n-propyl, isopropyl, n-butyl, isobutyl, sec-butyl, t-butyl, n-pentyl, isopentyl, neopentyl, n-hexyl, isohexyl, vinyl, allyl, cyclopropyl, cyclobutyl, cyclopentyl, cyclohexyl, cyclopentenyl, cyclohexenyl, cyclopentadienyl, cyclohexadienyl, phenyl, hydroxyethyl (HO—CH$_2$CH$_2$—), ethyloxy (CH$_3$CH$_2$—O—), aminomethyl (e.g., H$_2$N—CH$_2$—), aminoethyl (e.g., H$_2$N—CH$_2$CH$_2$—), methylamino (e.g., CH$_3$NH—), ethylamino (e.g., CH$_3$CH$_2$NH—), N-methyl-aminomethyl (e.g., HN(CH$_3$)—CH$_2$—), N-methyl-aminoethyl (e.g., HN(CH$_3$)—CH$_2$CH$_2$—), N,N-dimethyl-aminomethyl (e.g., (CH$_3$)$_2$N—CH$_2$—), N,N-dimethyl-aminoethyl (e.g., (CH$_3$)$_2$N—CH$_2$CH$_2$—), dimethylamino (e.g., (CH$_3$)$_2$N—), carboxamide (—C(O)NH$_2$), N-methylcarboxamide (—C(O)NH(CH$_3$)), and N,N-dimethylcarboxamide (—C(O)N(CH$_3$)$_2$). Where $R^4$ is repeated in a group (e.g., —NR$^4$$_2$), $R^4$ can be the same or different (i.e., $R^4$ is independently selected within the same group and between different groups).

In the case of $R^1$ being a heterocyclic ring, the heterocyclic ring may be bound via one of its ring carbon atoms or by one of its ring heteroatoms to the carbon atom shown in Formula (1). Similarly, in the case of $R^1$ containing a substituting group $R^4$, the group $R^4$ may be bound to a ring carbon atom or a ring heteroatom of $R^1$.

In some embodiments, the cyclic group of $R^1$ is directly attached to the carbon atom shown in Formula 1. In other embodiments, the cyclic group of $R^1$ is substituted with one or more linkers that link the cyclic group with the shown carbon atom. The linker is generally no more than six atom lengths (in particular embodiments, no more than five, four, three, two, or one atom length). The linker can be any of the linkers described above, or in particular, for example, —R$^4$—, —C(O)—, —C(O)R$^4$—, —NR$^4$—, —C=NR$^4$—, —N=NR$^4$—, —C=NR$^4$—, —C=N—NR$^4$—, —O—, —S—, —C(O)NR$^4$—, —NR$^4$C(O)R$^4$—, —C(O)O—, —C(O)OR$^4$—, —NR$^4$C(O)NR$^4$—, —NR$^4$C(O)OR$^4$—, —SO$_2$R$^4$—, or a linked combination thereof, wherein $R^4$ in the foregoing examples is an acyclic hydrocarbon group containing up to six carbon atoms. Some examples of —R$^4$— linkers include methylene (—CH$_2$—), ethylene (—CH$_2$CH$_2$—), 1,2-propylene (—CH$_2$C(CH$_3$)H—), trimethylene (—CH$_2$CH$_2$CH$_2$—), and vinylene (—CH=CH—). Some examples of —C(O)R$^4$— linkers include —C(O)CH$_2$— and —C(O)CH$_2$CH$_2$—. Some examples of —NR$^4$— linkers include —NH—, —N(CH$_3$)—, —N(CH$_2$CH$_3$)—, —N(iPr)—, —N(cyclopentyl)-, and —N(phenyl)-. Some examples of —C=NR$^4$-linkers include —C=N—CH$_2$—, —C=N—CH$_2$CH$_2$—, and —C=N—CH=CH—.

In one set of embodiments, $R^2$ in Formula (1) can be selected from any of the cyclic groups described above for $R^1$. In the case of $R^2$ being a cyclic group, the cyclic group may (optionally) be attached to the carbonyl carbon or nitrogen atom shown in Formula (1) via any of the linkers described above under $R^1$. In particular embodiments, $R^2$ is, or includes, a monocyclic, bicyclic, or higher polycyclic aromatic or heteroaromatic group, such as any of these groups described above. The aromatic or heteroaromatic group can be unsubstituted, or alternatively, substituted with one or more polar or non-polar substituents described above under $R^1$. In further embodiments, $R^2$ is, or includes, a heteroaromatic group that includes at least one (e.g., one, two, three, or four) ring nitrogen atoms. In more particular embodiments, $R^2$ is, or includes, a monocyclic heteroaromatic group that includes at least one ring nitrogen atom, such as a 2-, 3-, or 4-pyridyl group, or a pyrrolyl, pyrazinyl, imidazolyl, or triazinyl group. In some embodiments, the aromatic or heteroaromatic group of $R^2$ is directly bound to the shown carbonyl group (when t is 1) or the shown nitrogen atom (when t is 0). In other embodiments, the aromatic or heteroaromatic group of $R^2$ is indirectly bound, via a linker (such as any of the linkers described above, as for $R^1$), to the shown carbonyl group (when t is 1) or the shown nitrogen atom (when t is 0). In the case of $R^2$ being a heteroaromatic group, $R^2$ may be bound to the shown carbonyl group (when t is 1) or the shown nitrogen atom (when t is 0) either directly or indirectly (via a linker) by a ring carbon atom or ring heteroatom of $R^2$. When t is 0, and $R^2$ is, or includes, a heteroaromatic group, the heteroaromatic group generally binds to the shown nitrogen atom by a carbon atom, located either on the heteroaromatic group or on a linker connecting the heteroaromatic group with the shown nitrogen atom.

In another set of embodiments, $R^2$ in Formula (1) is selected from acyclic hydrocarbon groups $R^5$ containing up to twelve carbon atoms. The acyclic hydrocarbon group $R^5$ (and hence, $R^2$) can be any of the saturated or unsaturated, straight-chained or branched, and heteroatom-unsubstituted or heteroatom-substituted hydrocarbon groups described above under R and having up to twelve carbon atoms. In some embodiments, $R^2$ is selected from acyclic hydrocarbon groups $R^5$ containing up to six, seven, eight, nine, ten, eleven, or twelve carbon atoms, or more particularly, straight-chained or branched alkyl or alkenyl groups containing up to six, seven, eight, nine, ten, eleven, or twelve carbon atoms. In different embodiments, $R^5$ (and hence, $R^2$) is an acyclic hydrocarbon (or more particularly, alkyl or alkenyl) group containing one, two, three, four, five, six, seven, eight, nine, ten, eleven, or twelve carbon atoms, or a number of carbon atoms within a range bounded by any two of the foregoing numbers. In particular embodiments, $R^5$ (and hence, $R^2$) is a straight-chained or branched hydrocarbon (or more particularly, alkyl or alkenyl) group containing one, two, three, four, five, or six carbon atoms. In some embodiments, $R^2$ is a hydrocarbon group $R^5$ only when t is 1.

The group $R^3$ in Formula (1) can be a hydrogen atom or a hydrocarbon group containing up to six carbon atoms. In different embodiments, the hydrocarbon group of $R^3$ contains one, two, three, four, five, or six carbon atoms or a number of carbon atoms within a range therein. The hydrocarbon group $R^3$ may be saturated or unsaturated, straight-chained or branched, cyclic or acyclic, and may be heteroatom-unsubstituted or heteroatom-substituted. Some particular examples of $R^3$ include methyl, ethyl, n-propyl, isopropyl, n-butyl, isobutyl, sec-butyl, t-butyl, n-pentyl, isopentyl, neopentyl, n-hexyl, isohexyl, vinyl, allyl, cyclopropyl, cyclobutyl, cyclopentyl, cyclohexyl, cyclopentenyl, cyclohexenyl, cyclopentadienyl, cyclohexadienyl, phenyl, hydroxyethyl (HO—CH$_2$CH$_2$—), aminomethyl (e.g., H$_2$N—CH$_2$—), aminoethyl (e.g., H$_2$N—CH$_2$CH$_2$—), N-methyl-aminomethyl (e.g., HN(CH$_3$)—CH$_2$—), N-methyl-aminoethyl (e.g., HN(CH$_3$)—CH$_2$CH$_2$—), N,N-dimethyl-aminomethyl (e.g., (CH$_3$)$_2$N—CH$_2$—), N,N-dimethyl-aminoethyl (e.g., (CH$_3$)$_2$N—CH$_2$CH$_2$—), carboxamide (—C(O)NH$_2$), N-methylcarboxamide (—C(O)NH(CH$_3$)), and N,N-dimethylcarboxamide (—C(O)N(CH$_3$)$_2$).

In some embodiments, $R^2$ and $R^3$ are not interconnected, while in other embodiments, $R^2$ and $R^3$ are interconnected to form a cyclic structure. When t is 0, the cyclic structure is a cyclic amine. When t is 1, the cyclic structure is a cyclic amide. $R^2$ and $R^3$ can form an interconnected structure by replacing a hydrogen atom from each of $R^2$ and $R^3$ with a bond connecting $R^2$ and $R^3$. A double bond can also be included in said cyclic structure by replacing four hydrogen atoms from $R^2$ and $R^3$ with a double bond connecting $R^2$ and $R^3$. In particular embodiments, the group —NR$^2$R$^3$ (i.e., when t is 0), forms a saturated or unsaturated cyclic amine containing up to six ring carbon atoms. When $R^2$ and $R^3$ are hydrocarbon groups without heteroatoms, the resulting cyclic amine contains only one nitrogen ring atom as a heteroatom. Some examples of such cyclic amine groups when $R^2$ and $R^3$ are interconnected include pyrrolidinyl, piperidinyl, azepanyl, and unsaturated forms thereof (e.g., pyridinyl and pyrrolyl). When $R^2$ and $R^3$ are hydrocarbon groups with one or more heteroatoms, the resulting cyclic amine includes the shown nitrogen atom as a ring heteroatom, along with one or more ring heteroatoms provided by $R^2$ and/or $R^3$. Thus, when $R^2$ and $R^3$ are interconnected, $-NR^2R^3$ can represent, for example, an imidazolyl, pyrazolyl, piperazinyl, pyrazinyl, pyrimidinyl, triazinyl, oxazolyl, morpholinyl, indolyl, thiazolyl, quinolinyl, isoquinolinyl, or other such groups containing two or three ring nitrogen atoms, or one or two ring nitrogen atoms along with one or two other ring heteroatoms. The resulting interconnection results in a monocyclic, bicyclic, tricyclic, or higher polycyclic ring or ring system. Analogous cyclic structures that contain a ring amide group can result if $R^2$ and $R^3$ are interconnected when t is 1, e.g., butyrolactam and valerolactam rings.

The groups $R^6$ and $R^7$ in Formula (1) are independently selected from hydrogen atom, hydrocarbon groups containing up to three carbon atoms, halogen atoms, and polar groups, such as those selected from $-C(O)R^4$, $-NR^4_2$, $-OR^4$, $-NO_2$, $-C(O)NR^4_2$, $-NR^4C(O)R^4$, $-C(O)OR^4$, $-OC(O)R^4$, $-OC(O)NR^4_2$, $-NR^4C(O)NR^4_2$, $-NR^4C(O)OR^4$, $-SO_2R^4$, and nitrile, wherein $R^4$ is, independently, a hydrogen atom or an acyclic hydrocarbon group containing up to six carbon atoms (i.e., one, two, three, four, five, or six carbon atoms or a number of carbon atoms within a range therein). The polar group may (optionally) be attached to the ring carbon atom to which it is attached in Formula (1) by a methylene linking group, e.g., $-CH_2-C(O)OR^4$. In particular embodiments, the polar group is selected from $-C(O)OH$, $-OH$, halogen, and nitro group, as well as methylene-linked versions thereof (e.g., $-CH_2-COOH$ or $-CH_2-OH$).

In a first embodiment, one or both of $R^6$ and $R^7$ are hydrogen atoms. In a second embodiment, one or both of $R^6$ and $R^7$ are independently selected from hydrocarbon groups containing up to three carbon atoms. In a third embodiment, one or both of $R^6$ and $R^7$ are independently selected from halogen atoms. In a fourth embodiment, one or both of $R^6$ and $R^7$ are independently selected from polar groups and methylene-linked versions thereof.

Some exemplary compounds according to Formula (1) are provided as follows:

(a)
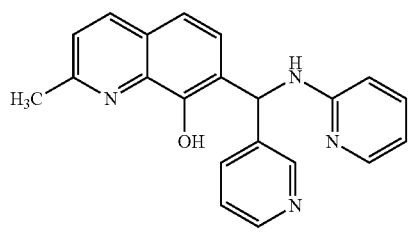

(b)
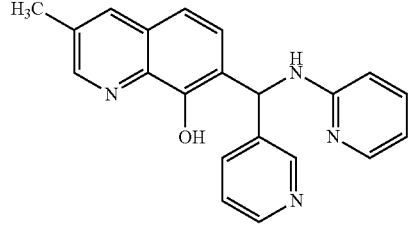

(c)
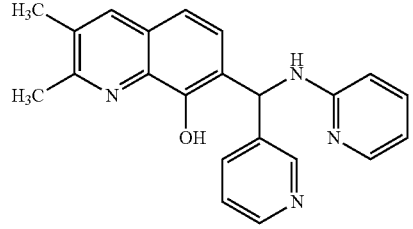

(d)
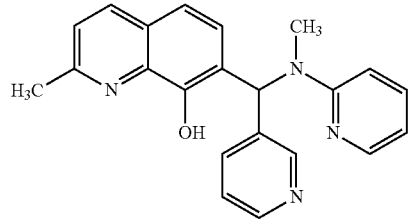

(e)
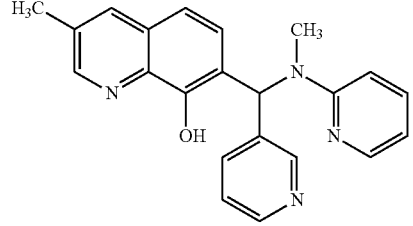

(f)
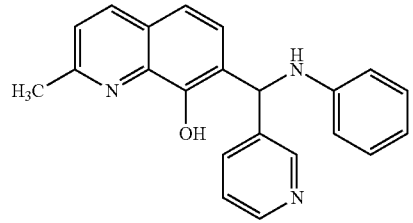

(g)
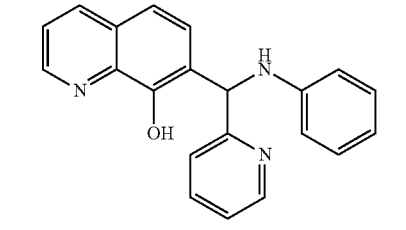

(h)
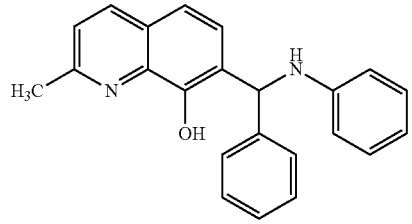

-continued
(i)
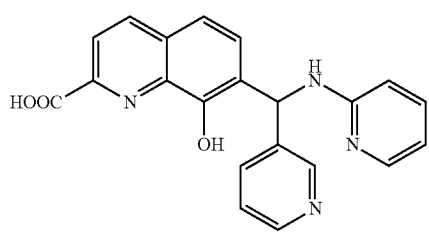
(j)
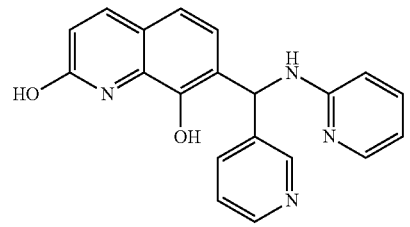
(k)
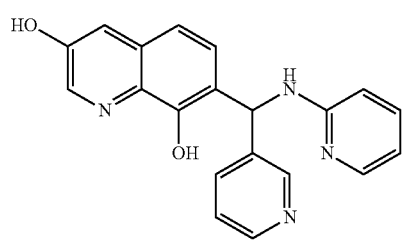
(l)
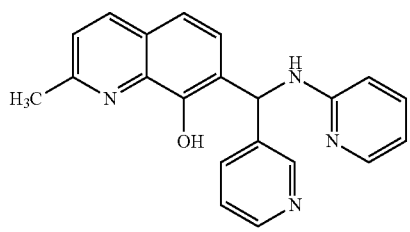
(m)
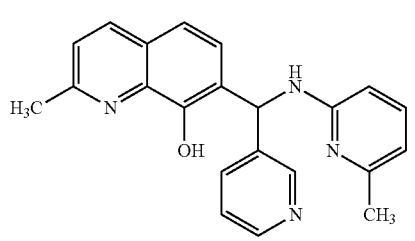
(n)
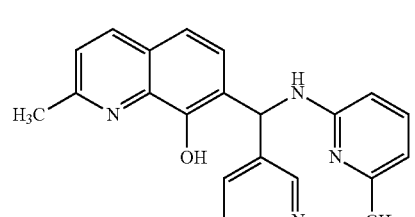
(o)
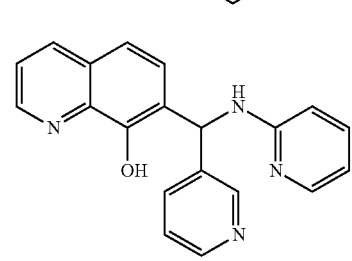
-continued
(p)
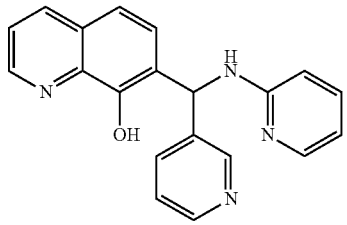
(q)
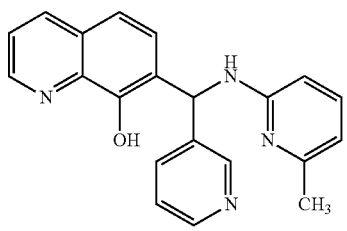
(r)
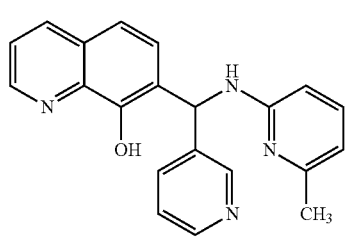
(s)
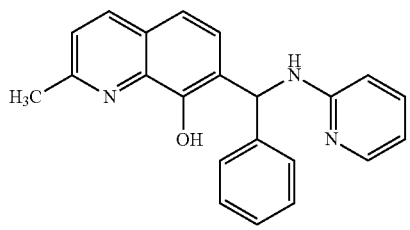
(t)
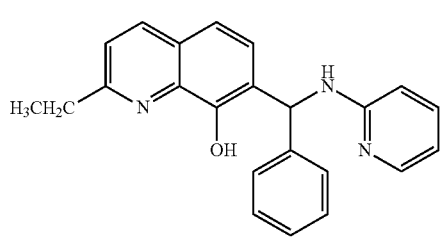
(u)
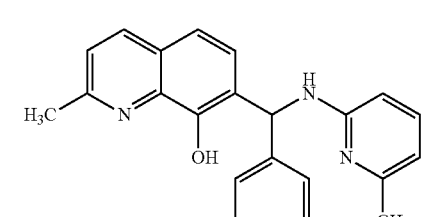
(v)
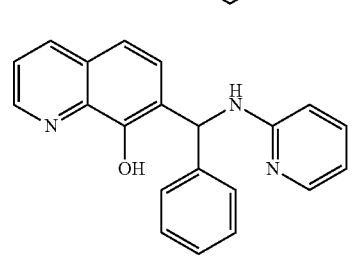

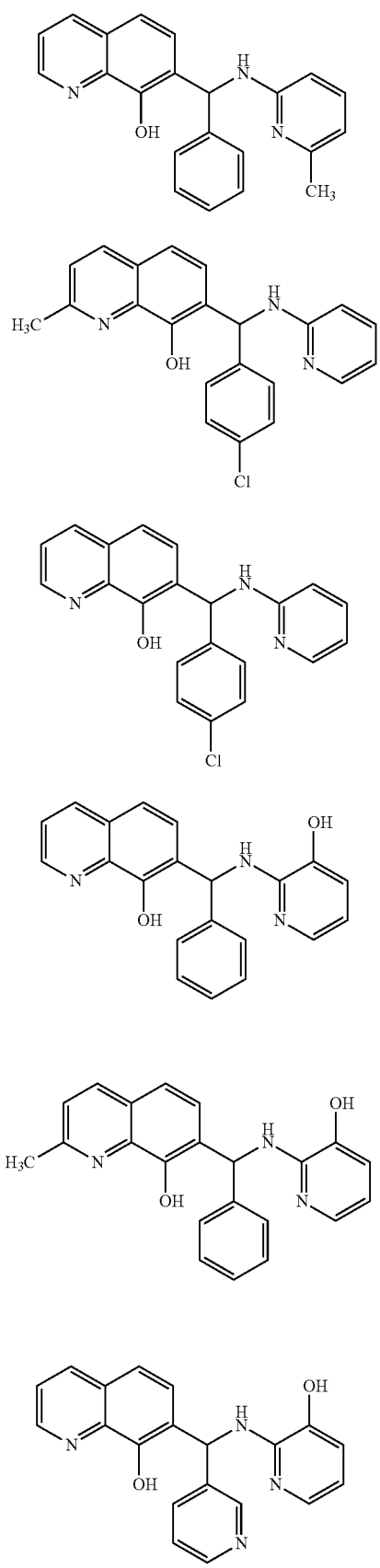

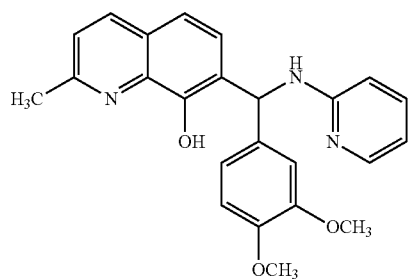
(ai)
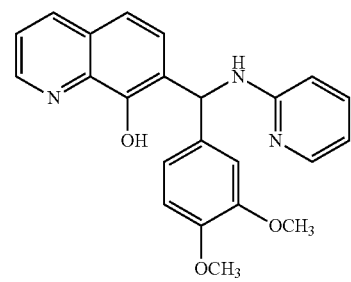
(aj)
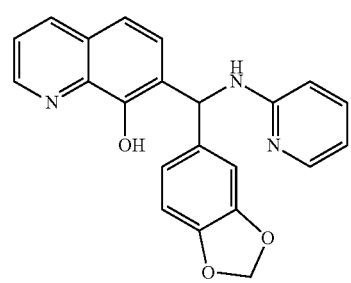
(ak)
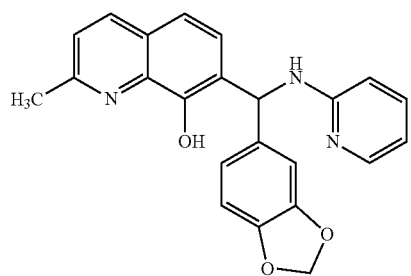
(al)
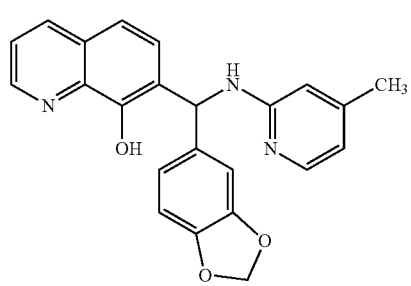
(am)
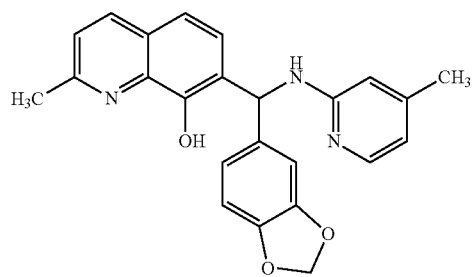
(an)
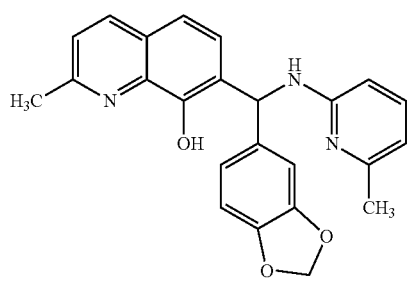
(ao)
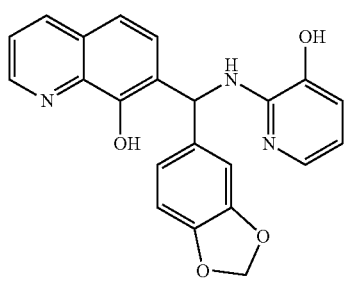
(ap)
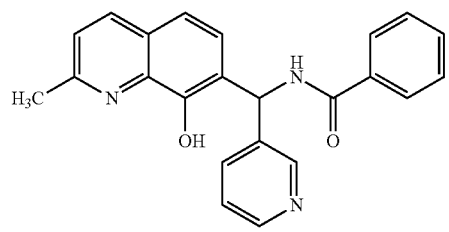
(aq)
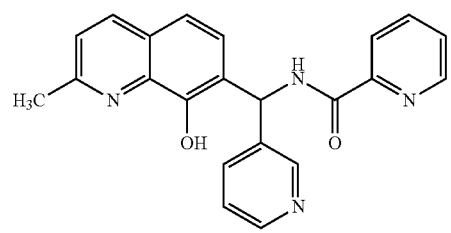
(ar)
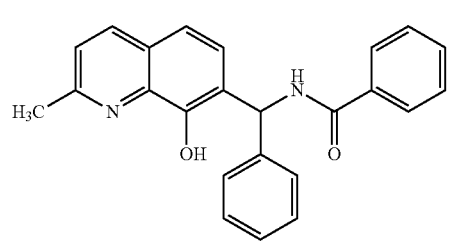
(as)

-continued
(at)
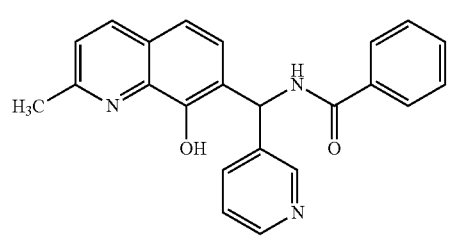
(au)
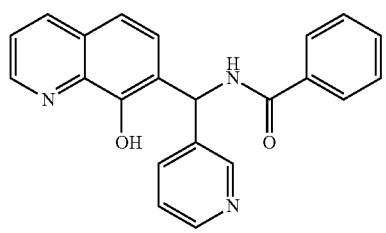
(av)
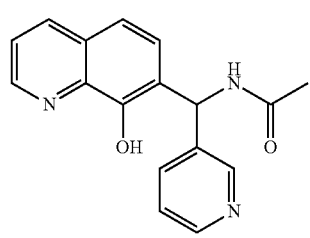
(aw)
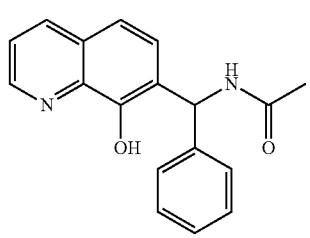
(ax)
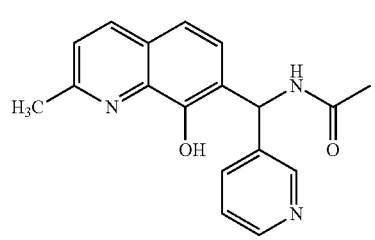
(ay)
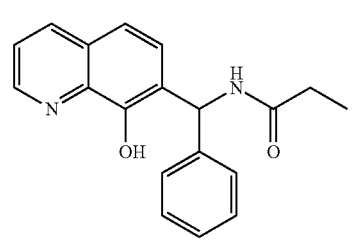
(az)
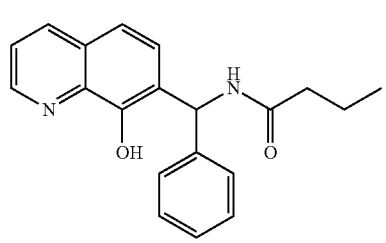
-continued
(ba)
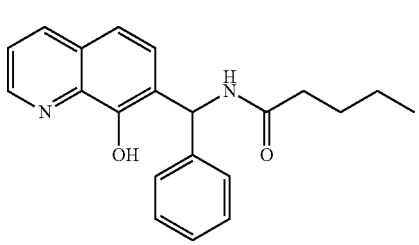
(bb)
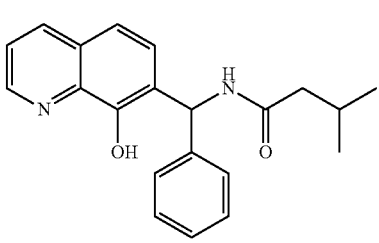
(bc)
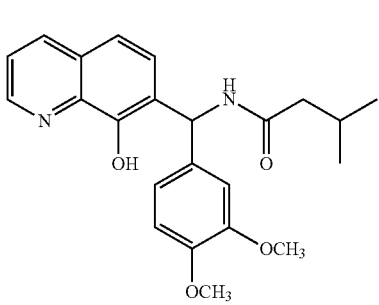
(bd)
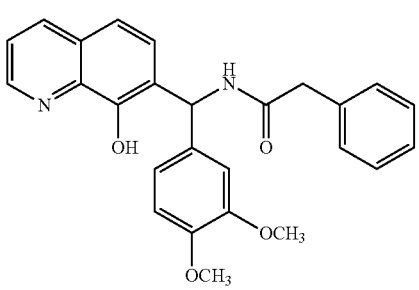
(be)
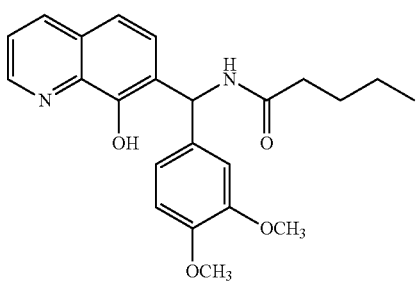
(bf)
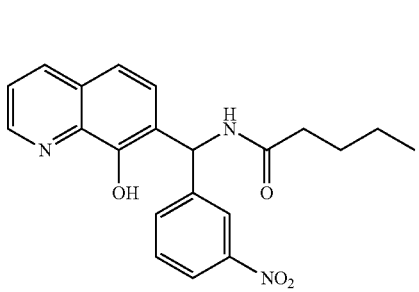

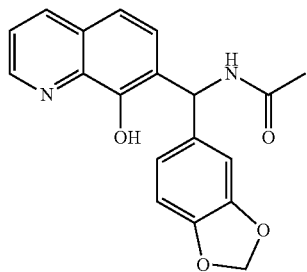

(bg)

The 8-hydroxyquinolinyl compounds described herein can be synthesized by any methods known in the art. Many of the quinolinyl derivatives described herein, in particular, can utilize the methodology described in the art for their synthesis, along with appropriate modification as would be readily understood in the art. See, for example, N. C. Warshakoon, et al., *Bioorganic & Medicinal Chemistry Letters*, 16, pp. 5517-5522 (2006), the entire disclosure of which is incorporated herein by reference.

Numerous other synthetic methodologies are known and applicable herein, along with appropriate modification, for synthesizing a wide range of compounds encompassed by Formula (1). See, for example, N. C. Warshakoon, et al., *Bioorganic & Medicinal Chemistry Letters*, 16, pp. 5598-5601 (2006); J. K. Murray, et al., *J. Comb. Chem.*, 12, pp. 676-686 (2010); International Pub. WO 2007/070359; M. Frohn, et al., *Bioorganic & Medicinal Chemistry Letters*, 18, pp. 5023-5026 (2008); and *ACS Med. Chem. Lett.*, 1, pp. 526-529 (2010); the entire contents of which are herein incorporated by reference.

Some additional generic protocols applicable herein for preparing the quinolinyl or indolyl compounds described herein, along with appropriate modification, are provided in the following synthetic schemes. In the following synthetic schemes, the designations $R^1$ and $R^2$ do not relate to the same named groups elsewhere in the remainder of this specification; rather, the generic groups included in the following schemes should be considered to have a scope corresponding to groups in equivalent positions found in generic Formula (1), or alternatively, as variable hydrocarbon groups or reactive groups understood by one skilled in the art to be appropriate for the indicated reaction.

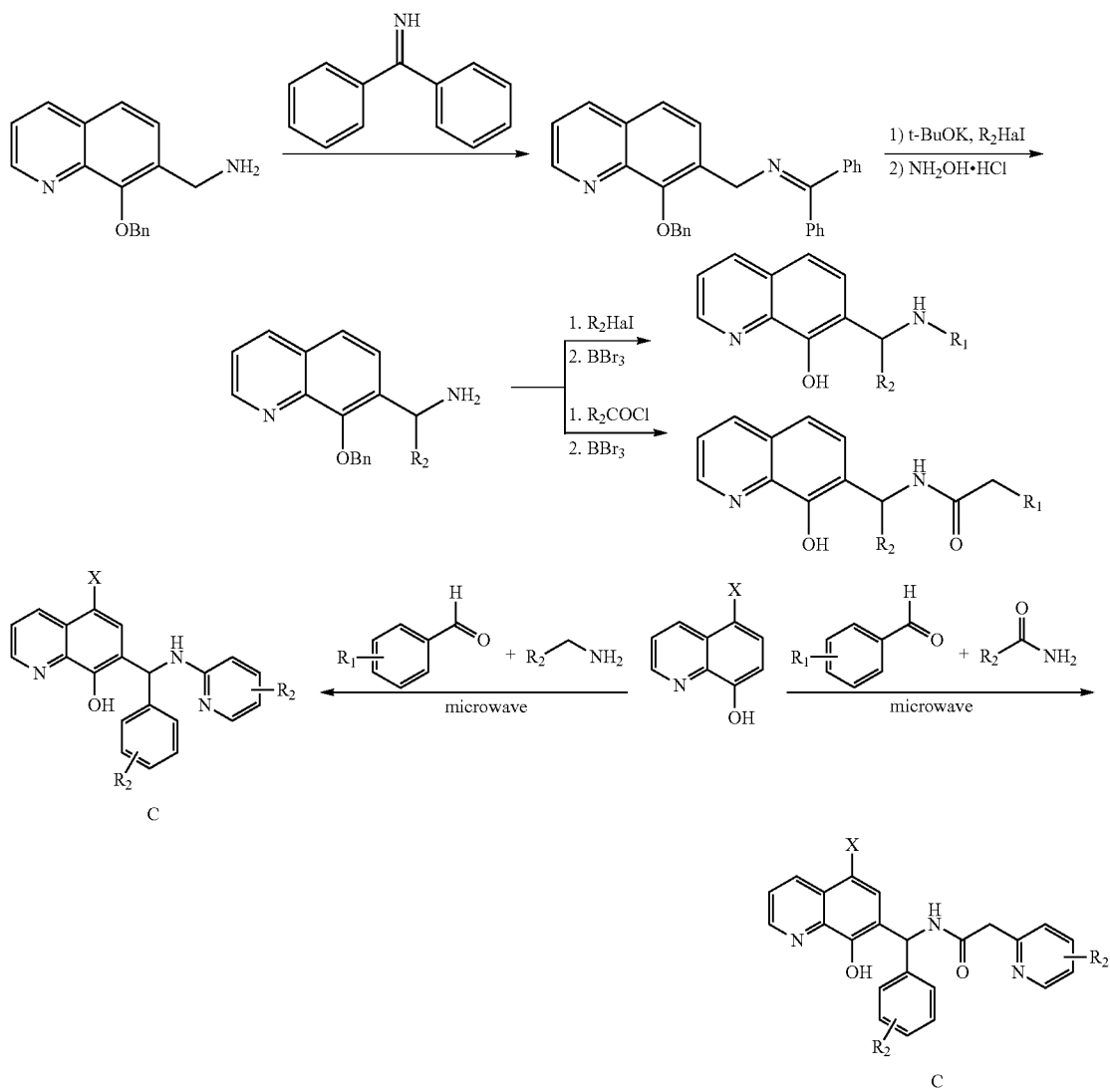

-continued

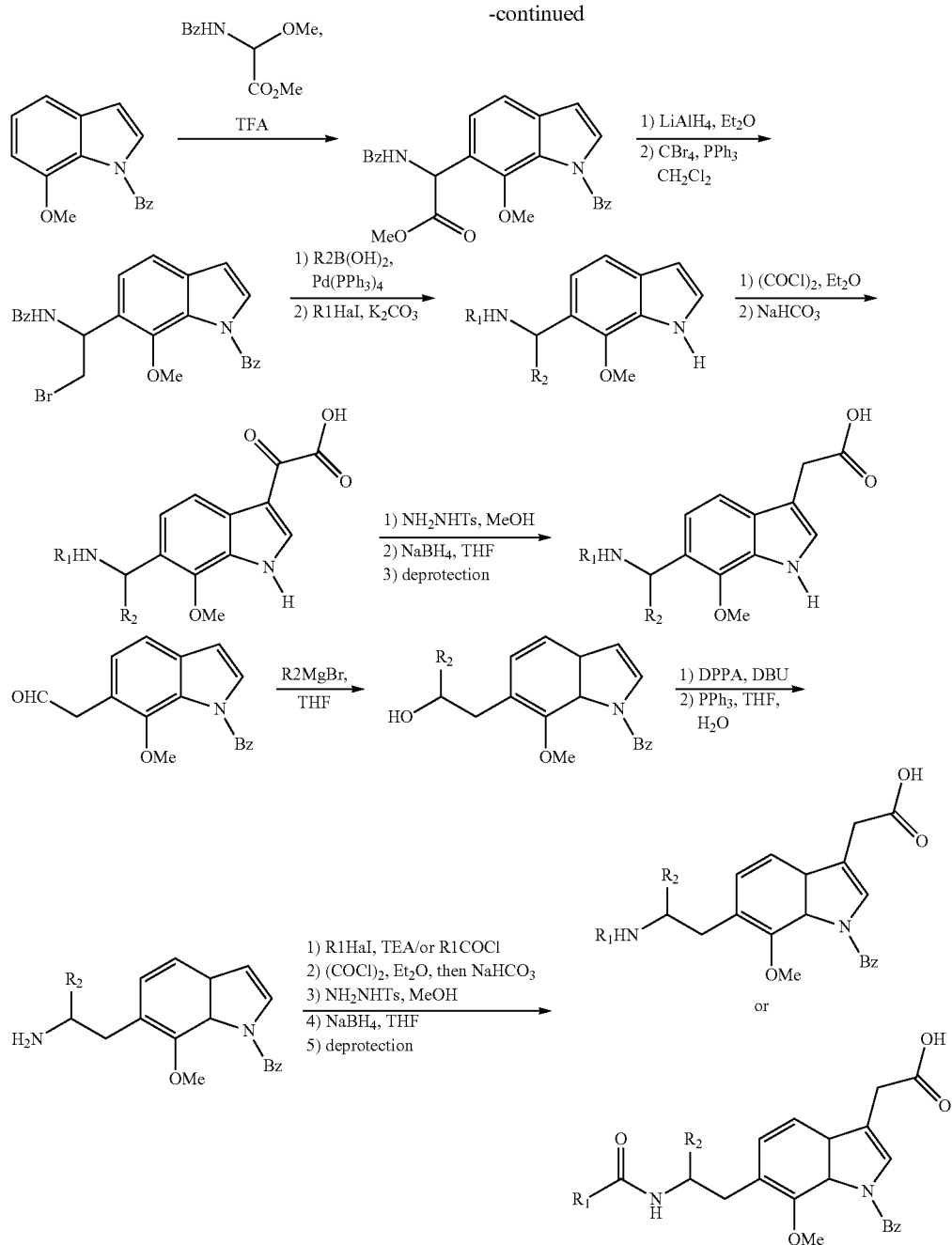

In another aspect, the invention is directed to a pharmaceutical composition that contains any one, two, or more of the above HIF PHD-inhibiting compounds in a pharmaceutically acceptable vehicle (i.e., excipient). The pharmaceutical composition can also be formulated together with one or more medications that improve the overall efficacy of the pharmaceutical composition and/or reduces or avoids side effects.

The active ingredient(s) and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, such as, for example, tablets, capsules, powders, granules, or pastes for application to the tongue, aqueous or non-aqueous solutions or suspensions, drenches, or syrups; (2) parenteral administration, such as, for example, by subcutaneous, intramuscular or intravenous injection as provided by, for example, a sterile solution or suspension; (3) topical application, such as, for example, provided by a cream, ointment, or spray applied to the skin, lungs, or mucous membranes; or (4) intravaginally or intrarectally, such as, for example, as a pessary, cream or foam; (5) sublingually or buccally; (6) ocularly; (7) transdermally; or (8) nasally.

The phrase "pharmaceutically acceptable" refers herein to those compounds, materials, compositions, and/or dosage forms which are, within the scope of sound medical judgment, suitable for administration to a subject. The phrase "pharmaceutically acceptable excipient" as used herein refers to a pharmaceutically-acceptable material, composition, or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic composition for administration to the subject. Each excipient should be "acceptable" in the sense of being compatible with the other ingredients of the formulation and not injurious to the subject.

Some examples of materials that can serve as pharmaceutically-acceptable excipients, particularly for liquid forms, include sugars (e.g., lactose, glucose, sucrose, and oligosaccharides, such as sucrose, tetralose, lactose, or dextran); starches (e.g., corn and potato starch); cellulose and its derivatives (e.g., sodium carboxymethyl cellulose, ethyl cellulose and cellulose acetate); gelatin; talc; waxes; oils (e.g., peanut oil, cottonseed oil, safflower oil, sesame oil, olive oil, corn oil and soybean oil); glycols (e.g., ethylene glycol, propylene glycol, and polyethylene glycol); polyols (e.g., glycerin, sorbitol, and mannitol); esters (e.g., ethyl oleate and ethyl laurate); agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Diluents increase the bulk of a solid pharmaceutical composition, and may make a pharmaceutical dosage form that is easier for the patient or caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the subject's stomach may be increased by the addition of a disintegrant to the composition. Some examples of disintegrants include alginic acid, carboxymethylcellulose calcium, carboxymethylcellulose sodium (e.g. Ac Di Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Numerous other auxiliary agents, commonly known in the art, may be included in the pharmaceutical composition. Some examples of these other auxiliary agents include glidants for improving the flowability of a non-compacted solid composition (e.g., colloidal silicon dioxide, magnesium trisilicate, powdered cellulose, starch, talc and tribasic calcium phosphate); lubricants to reduce adhesion during processing (e.g., magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate); liquid carriers or dispersants, such as water, vegetable oil, alcohol, polyethylene glycol, propylene glycol or glycerin; emulsifying agents, such as gelatin, egg yolk, casein, cholesterol, acacia, tragacanth, chondrus, pectin, methylcellulose, carbomer, cetostearyl alcohol and cetyl alcohol; viscosity-enhancing agents to improve the mouthfeel of the product and/or coat the lining of the gastrointestinal tract (e.g., acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum); sweetening agents, such as sorbitol, saccharin, sodium saccharin, sucrose, aspartame, fructose, mannitol and invert sugar; flavoring agents and flavor enhancers, such as maltol, vanillin, ethyl vanillin, menthol, citric acid, fumaric acid, ethyl maltol and tartaric acid; preservatives and chelating agents, such as alcohol, sodium benzoate, butylated hydroxy toluene, butylated hydroxyanisole and ethylenediamine tetraacetic acid; buffers, such as gluconic acid, lactic acid, citric acid or acetic acid, sodium gluconate, sodium lactate, sodium citrate or sodium acetate; salts; buffering agents; surfactants; solubilizers (e.g., glycerol); and stabilizers (e.g., an amino acid, such as glycine). The selection of excipients and the amounts used may be readily determined by the formulation scientist based upon experience and consideration of standard procedures and reference works in the field.

In a particular aspect, the invention is directed to methods for treating a patient suffering from neural cell injury (e.g., brain or spinal cord injury) by administering to the patient an effective amount of any of the HIF PHD-inhibiting or ATF4-inhibiting compounds described above, typically by administration of a pharmaceutical composition containing one or more of the compounds described above. The treatment may be administered when neural cell injury is evident, or alternatively, as a preventative treatment before neural cell injury is evident.

In a further aspect, the method may also be directed to promoting recovery of neural cell function in a patient that has suffered neural cell injury or death in connection with brain or spinal cord injury. In some embodiments, the brain injury, in particular, can be a result of or associated with intracerebral hemorrhage (ICH). The method includes administering to the patient in need thereof an effective amount of a compound according to Formula (1) that reduces ATF4 activity to the extent that neural cell function is sufficiently recovered. In such treatment, the compound can function as a neuroprotective agent, wherein the term "neuroprotective agent" limits neural dysfunction and/or death in the central nervous system (CNS) and peripheral nervous system (PNS) by inducing neuroprotective effects. Neuroprotective effects include maintaining neuronal viability, which includes maintaining integrity of normal cellular interactions and normal neural function. In some embodiments, the compound being administered mitigates ICH-induced sensorimotor, somatosensory, or motor dysfunction. Stated differently, in some embodiments, the compound being administered improves sensorimotor, somatosensory, or motor skills of the patient being treated. In other embodiments, the compound being administered reduces hematoma size and/or edema (brain swelling).

The brain injury considered herein for treatment may be any type of brain injury. The brain injury can be, for example, a primary or secondary brain injury, a focal or diffuse brain injury, or a traumatic, non-traumatic, neurotoxic-induced, or acquired brain injury. In the case of traumatic brain injury, the brain injury can be classified as, moderate, or severe traumatic brain injury.

In yet a further aspect, the method may also be directed to promoting synaptic plasticity in a patient suffering from neural cell injury, particularly brain or spinal cord injury. The method includes administering to the patient in need thereof an effective amount of a compound according to Formula (1) that reduces ATF4 activity to the extent that synaptic plasticity is improved.

In still another aspect, the invention relates to a method for limiting oxidative stress in a patient suffering from neural cell injury, particularly brain or spinal cord injury, in which oxidative stress is a mediator of the injury. The method includes administering to the patient in need thereof an effective amount of a compound according to Formula (1) that reduces ATF4 activity.

A compound is identified as a drug candidate with activity as a neuroprotective agent by determining whether the compound reduces the activity of (activating transcription factor 4) ATF4, which is also referred to as CREB2. ATF4 is a stress response transcription factor that is expressed constitutively only at low concentrations, but gets rapidly induced under particular cell stress conditions. Once translated, ATF4 protein binds to the promoter regions of an array of different target genes including many that are involved in amino acid metabolism and redox control.

As used herein, "ATF4" refers to human ATF4 having a nucleic acid sequence and amino acid sequence as set forth in GenBank accession numbers NM_182810, NM_001675, and CU012942. The term "ATF4" further includes a nucleic acid and amino acid sequence having at least 95 percent homology (i.e., identity) to the sequences set forth in GenBank, as determined by methods known in the art.

A compound that "reduces" ATF4 activity refers to a compound that decreases a measurable level of ATF4 activity in a given assay in the presence of the compound, relative to a measurable level of ATF4 activity in the absence of the compound when tested under the same conditions.

Activity is generally considered reduced according to the invention if it is reduced at least about 10%, preferably, at least about 20%, more preferably at least about 30%, even more preferably at least about 40%, and most preferably at least about 50% or more than in the absence of the compound. Optimally, at least about 70%, more optimally at least about 85%, and most optimally 100% of the ATF4 activity in a cell is reduced in a neural cell.

"ATF4 activity", as used herein, can be reduced by any mechanism. For example, ATF4 activity could be reduced by reducing transcriptional induction of its cognate messenger RNA (mRNA), decreasing stability of ATF4 mRNA, decreasing translation of ATF4 mRNA into protein, decreasing stability of ATF4 protein, decreasing ATF4 activity (in the presence or absence of decreased protein), inhibiting binding of ATF4 to its target DNA, or any other mechanism.

In one embodiment, the act of determining whether a compound reduces ATF4 activity includes providing a cell expressing ATF4, contacting the cell with the compound, and measuring the level of ATF4 activity in the cell, wherein a decrease in the level of ATF4 activity in the cell in the presence of the compound indicates that the compound is able to reduce ATF4 activity.

The act of determining whether a compound reduces ATF4 activity in a given cell may also be determined indirectly by determining either the amount of ATF4 mRNA or the amount of ATF4 protein produced by the cell before and after contact with the compound. The level of mRNA transcribed from the ATF4 gene or the level of ATF4 protein encoded by the ATF4 gene in the cell may be determined by quantitative methods known in the art. Any cell that expresses ATF4 may be used in the method of the invention. Expression may occur in the cell in vitro or in vivo.

Examples of a suitable cell that expresses ATF4 in vitro include a neural cell and a cell from the mouse hippocampal cell line HT22-ATF4-Puro, and several cancer cell lines as disclosed in Fels, et al. 2006, *Cancer Biol. Ther.* 5:723-728; Shringarpure, et al. 2006, *Br. J. Haematol.* 134:145-156; Torigoe, et al. 2005, *Curr. Med. Chem. Anticancer Agents.* 5:15-27; Park, et al. 2004, *J. Natl. Cancer Inst.* 96:1300-1310; Tanabe, et al., 2003, *Cancer Res.* 63:8592-8595. The cell may be derived from any mammal, such as a mouse, rat, or human. The cell is typically derived from a human.

Cells that express ATF4 in vitro may require a known compound to induce ATF4 expression, such as thapsigargin and tunicamycin. Accordingly, in one embodiment, the level of ATF4 activity in the cell in the presence of the test compound is measured in relation to a level of ATF4 activity in the cell contacted with thapsigargin or tunicamycin.

Examples of a suitable cell that expresses ATF in vivo include neural cells. Any neural cell may be involved in the methods of the invention. As used herein, a "neural cell" includes nerve cells (i.e., neurons, e.g., uni-, bi-, or multi-polar neurons) and their precursors and glial cells (e.g., macroglia such as astrocytes, oligodendrocytes, ependymal cells, radial glia, Schwann cells, Satellite cells, and microglia) and their precursors. Microglia are specialized macrophages capable of phagocytosis that protect neurons of the central nervous system. The term "precursor" refers to cells which are capable of developing into a specific cell type. For example, a neural cell precursor is a cell which is capable of developing into a mature neural cell (i.e., a cell having the characteristic morphology and function of a neural cell).

Examples of cells that may undergo neural cell injury or death include cells of the central nervous system (CNS) or peripheral nervous system (PNS), including neurons, ganglia, Schwann cells, astrocytes, oligodendrocytes, microglia cells, endothelial cells, immune cells (e.g., macrophages, T cells, B cells, and neutrophils), etc. Suitable cells include those of mammals, e.g., laboratory animals, such as mice, rats, and other rodents; monkeys, baboons, and other primates, etc. In one embodiment, the cell is a human cell.

The act of determining whether a compound reduces ATF4 activity includes contacting the cell expressing ATF4 with the compound. The term "contacting" refers to directly or indirectly bringing the cell and the compound together in physical proximity. The contacting may be performed in vitro or in vivo. For example, the cell may be contacted with the compound by delivering the compound into the cell through known techniques, such as microinjection, injecting the compound into the bloodstream of a mammal, and incubating the cell in a medium that includes the compound.

The act of determining whether a compound reduces ATF4 activity further includes measuring the level of ATF4 activity in the cell. The level of ATF4 may be measured by any method known in the art, including for example, PCR analysis, RT-PCR, Northern blot, Western blot, immunohistochemistry, ELISA assays, luciferase reporter assays, etc. For example, the level of ATF4 activity may be assessed by measuring the level of induction of a reporter gene (e.g., luciferase) that is operably linked to the ATF4 gene.

The level of ATF4 activity may also be assessed by detecting the level of activity of a gene that is targeted by ATF4. Genes that are targeted by ATF4 include, for example, heme oxygenase 1, stanniocalcin2, osteocalcin, gadd153/CHOP, and TRB3. Typically, the level of ATF4 activity in a given cell is measured in the presence of and in the absence of the test compound.

Identifying drug candidates typically involves multiple phases. During the early stages, a library of compounds is typically screened or tested in vitro for binding to and/or biological activity at ATF4. The compounds that exhibit activity ("active compounds" or "hits") from this initial screening process are then typically tested through a series of other in vitro and in vivo tests to further characterize the neuroprotective activity of the compounds. The in vivo tests at this phase may include tests in non-human mammals, such as those mentioned above. If a compound meets the criteria for continued development as a drug following in vitro and in vivo tests, the compound may be selected as a candidate for testing in humans. A progressively smaller number of test compounds at each stage are typically selected for testing in the next stage. The series of tests eventually leads to one or a few drug candidates being selected to proceed to testing in human clinical trials. The human clinical trials may include studies in a human suffering from a medical condition that can be treated or prevented by reducing ATF4 activity. Suitable drug candidates for the methods described herein are preferably, but not necessarily, approved by a governmental entity responsible for approving drugs for human use (e.g., the United States Food and Drug Administration, and comparable national and regional agencies outside the United States).

In a particular aspect, the invention relates to a method for reducing ATF4 activity in one or more neural cells in a patient suffering from neural cell injury, particularly brain or spinal cord injury. The method includes administering to the patient an effective amount of any one or more compounds described above under Formula (1) to the extent that one or more adverse neural effects associated with brain or spinal cord injury are mitigated. The administration may, in some embodiments, include co-administration of one or more other compounds active for reducing ATF4 activity, such as Thimerosal; Gambogic Acid; Anthothecol; Disulfuram; Pyrithione Zinc; Thiram; Tomatine; Dihydrogambogic Acid; Trifluoperazine Hydrochloride; Alexidine Hydrochloride; Phenylmercuric Acetate; Pristimerin; Aklavine Hydrochloride; 6,3'-Dimethoxyflavone; Tetrachloroisophthalonitrile; Actinomycin D; Cedrelone; Pyrromycin; Mitoxanthrone Hydrochloride; Tyrothricin; Selinidin; Gentian Violet; Clofoctol; Aminacrine; Penicillic Acid; Byssochlamic Acid; Hieracin; Atranorin; Dihydrojasmonic Acid; Deltaline; Azaserine; Sodium Fluoroacetate; Thalidomide; Neomycin Sulfate; Camptothecin; Trimedlure (5-Cl Isomer Present); Chlorguanide Hydrochloride; Benzo[a]pyrene; Hycanthone; Methotrexate; Dihydrorotenone; Galanthamine Hydrobromide; Ipraflavone; 5,7-Dichlorokynurenic Acid; Haematoporphyrin Dihydrochloride; Osthol; 1r,2s-Phenylpropylamine; 2,4-Dinitrophenol; Bromopride; Isorotenone; Lycorine; Halcinonide; 7-Desacetoxy-6,7-Dehydrogedunin; 6-Aminonicotinamide; 6alpha-methylprednisolone acetate; Teniposide; 1-Methylxanthine; Mercaptopurine; Tripelennamine Citrate; 9-Amino-1,2,3,4-Tetrahydroacridine Hydrochloride; Beta-Dihydrorotenone; Acivicin; Hydroxytacrine Maleate; or Cetylpyridinium Chloride.

A patient in need of a method for reducing ATF4 activity in a neural cell includes, for example, a patient suffering from a memory deficit; a memory surfeit; a stroke; ischemia; trauma to the central nervous system or peripheral nervous system; epilepsy-related brain damage, poisoning with a neurotoxic compound, or radiation-induced brain damage; an infectious disease of the central nervous system or peripheral nervous system; a cancer of the central nervous system or peripheral nervous system; and/or a neurodegenerative disease or condition.

The method for reducing ATF4 is especially useful in a patient suffering from a neurodegenerative disease or condition. A neurodegenerative disease or condition includes, for example, Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, depression or a psychiatric disorder in which elements of cognition and memory have become disordered. The method for reducing ATF4 may be especially useful in a human suffering from dementia, which may be age-related dementia, dementia related to vitamin deficiency, or alcohol-related dementia.

A patient in need of a method for reducing ATF4 activity in a neural cell may also be a patient in need of any of the methods described herein that include administering to the patient an effective amount of a compound that reduces ATF4 activity. Such methods include, for example, protecting neural cells from neural cell injury or death, promoting recovery of neural cell function, promoting synaptic plasticity, and limiting oxidative stress.

In some embodiments, the method for reducing ATF4 activity by administering a compound that reduces ATF4 activity further includes prescribing or treating the patient with physical therapy, psychotherapy, or a combination thereof. Physical therapy includes treating disease, injury, or disability by physical and mechanical means, e.g., by massage, regulated exercise, water, light, heat, and electricity. Physical therapy may include robotic techniques, such as those described in Volpe B T et al (2005) *Robotics and Other Devices in the Treatment of Patients Recovering from Stroke. Current Neurology and Neuroscience Reports* 5:465-470. Conditions that can be treated with a combination of reducing ATF4 activity and physical therapy include, for example, muscular control, sport-related injuries, traumatic brain injury, stress incontinence, neurological conditions, such as stroke and multiple sclerosis, rehabilitation following amputation, and cardiopulmonary rehabilitation.

Psychotherapy refers to treating a mental or emotional disorder or related physical conditions by psychological means. Psychotherapy includes various therapy models used by clinical psychologists. Four major psychotherapy perspectives include psychodynamic, cognitive behavioral, existential-humanistic, and systems or family therapy. Psychotherapy models generally involve a formal relationship between the clinical psychologist and client. The client may be an individual, couple, family, or small group. Psychotherapies typically employ a set of procedures to form a therapeutic alliance, explore the nature of psychological problems, and encourage new ways of thinking, feeling, or behaving. Some conditions that can be treated with a method for reducing ATF4 activity and psychotherapy include, for example, anxiety disorders, such as those listed in the DSM-IV, including generalized anxiety disorder, panic disorder (with and without agoraphobia), agoraphobia without history of panic disorder, specific phobia, social phobia, obsessive-compulsive disorder, posttraumatic stress disorder, and acute stress disorder.

In other embodiments, the invention is directed to a method for protecting a neural cell from further neural cell injury or death in a patient who has suffered neural cell injury. The method includes administering to the patient an effective amount of a compound that reduces ATF4 activity to the extent that the patient is protected from further neural cell injury or death. The method more particularly refers to decreasing further neural cell injury or death in a neural cell, as compared to the likelihood of such injury or death in the absence of a compound that reduces ATF4 activity. Protecting a neural cell includes being able to impart neuroprotective effects, as described above.

A patient who has suffered a neural cell injury or death caused by a disease or disorder of the CNS or PNS may be susceptible to further neural cell injury or death. For example, a patient who has suffered a first neural cell injury or death due to stroke is typically more susceptible or has a greater likelihood of suffering additional neural cell injury or death after the first episode of stroke. The increase in susceptibility is relative to a patient who has not suffered a first neural cell injury or death.

In a further aspect, the invention relates to a method for promoting recovery of neural cell function in a patient that has suffered neural cell injury or death. The term "neural cell injury or death", as used herein, refers to any physical alteration, disruption, physical or chemical insult to a neural cell, or disease or disorder in which reducing ATF4 activity is desired. The neural cell injury or death may result in a partial or complete loss of an ability of the neural cell to properly function. The method includes administering to the patient an effective amount of a compound that reduces ATF4 activity to the extent that an improvement in neural cell function is achieved. The method increases the rate or extent of recovery of neural cell function following a neural cell injury or death, wherein the neural cell injury or death may result in a partial or complete loss of an ability of the neural cell to properly function (i.e., loss or diminishment of ability of the patient to perform a usual or expected activity or behavior). The improvement in recovery is in comparison to the rate or extent of such recovery, if any, in the absence of a compound of Formula (1) that reduces ATF4 activity. The method more particularly results in improving the recovery of neural cell function compared to such recovery, if any, in the absence of a compound that reduces ATF4 activity. The term "recovery of neural cell function", as used herein, refers to regaining, at least in part, the ability to perform a neural cell function properly, following a neural cell injury or death. Recovery can also refer to preservation of the ability of a neural cell to perform a function that it performed prior to a neural cell injury or death. The recovery of neural cell function may be due to partial or complete restoration of a structure of a neural cell that was subjected to a neural cell injury or death. The term "neural cell function" refers to any function, role, task, or activity performed by a normal neural cell. Neural cell functions include the ability to process and recall information; regulation of factors, hormones, proteins, or compounds relating to the CNS and PNS; stimulating release or uptake of endogenous chemicals; controlling of motor functions; receiving and processing sensory factors; maintaining consciousness, etc.

In yet a further aspect, the invention relates to a method for promoting synaptic plasticity in a patient in need thereof. The method includes administering to a patient in need thereof an effective amount of a compound that reduces ATF4 activity to the extent that an improvement in synaptic plasticity is achieved. The method increases or otherwise improves synaptic plasticity in a neural cell following neural cell injury or death. The method more particularly results in increasing synaptic plasticity as compared to such increase, if any, in the absence of a compound that reduces ATF4 activity. The term "synaptic plasticity" refers to the capacity of a neural cell to change its structure and/or function in response to a neural cell injury or death, environmental condition, experience, or ongoing CNS or PNS activity. Synaptic plasticity may involve the proliferation of neural cells, the growth or movement of neural cell processes and/or alterations in their shape. Synaptic plasticity may involve formation of new synaptic connections between or among neural cells, which may involve growth or movement of neural cells. Synaptic plasticity may further involve strengthening or weakening of existing synaptic connections.

In still another aspect, the invention relates to a method for limiting oxidative stress in a patient who has a condition in which oxidative stress is a mediator of neural cell injury. The method includes administering to the patient an effective amount of a compound that reduces ATF4 activity to the extent that oxidative stress is reduced. The term "limiting oxidative stress" refers to decreasing oxidative stress compared to such reduction of oxidative stress, if any, in the absence of a compound that reduces ATF4 activity. The term "oxidative stress" refers to a condition in which there is an overproduction of oxygen-free radicals or a deficiency in an antioxidant defense and repair mechanism, or both.

Disorders and diseases in which reducing ATF4 activity is desired for treatment include, for example, ischemia, neurodegenerative disease or condition, or stroke. Additional disorders and diseases in which reducing ATF4 activity is desired for treatment include, for example, traumatic disorders (including but not limited to brain injury, spinal cord injuries, spinal cord lesions, or other CNS pathway lesions), surgical nerve lesions, damage secondary to infarction, infection, exposure to toxic agents, malignancy, paraneoplastic syndromes, or patients with various types of neurodegenerative disorders of the central nervous system. The mammal suffering from neural cell injury or death is typically suffering from a disease or disorder in which reducing ATF4 activity is desired.

A mammal suffering from neural cell injury or death stemming from ischemia can also be treated in accordance with the methods of the invention. Ischemia generally refers to a condition of decreased blood flow to an organ, tissue and/or cell. The decrease in blood flow can be caused by, for example, constriction (e.g., hypoxemic vasoconstriction) or obstruction (e.g., clot, atherosclerotic plaque) of a blood vessel. Ischemia can occur in any cell, organ, and/or tissue. Examples of cells, organs, and/or tissues which can be subjected to ischemia include neuronal cells (e.g., neurons, ganglia, Schwann cells, astrocytes, oligodendrocytes and microglia), brain, spinal cord, intestinal cells, kidney cells, heart and cardiac muscle cells such as myocytes, etc.

A mammal suffering from a neurodegenerative disease or condition can also be treated in accordance with the methods of the invention. In some embodiments, the neurodegenerative disease or condition is an acute condition. Acute conditions generally occur as a result of trauma to a cell, tissue and/or organ of the nervous system. The trauma can, for example, partially or completely block blood flow to the cell, tissue and/or organ. Examples of acute neurodegenerative conditions include head injury and brain injury. A neurodegenerative disease or condition typically refers to a disorder characterized by gradual and progressive loss of cells, tissue and/or organ of the central or peripheral nervous system. Examples of such cells, tissues and organs include, for example, the brain, spinal cord, neurons, ganglia, Schwann cells, astrocytes, oligodendrocytes and microglia. Alternatively, the neurodegenerative disease or condition can be a chronic neurodegenerative condition. Examples of chronic neurodegenerative diseases and conditions include Parkinson's disease, Alzheimer's disease, Huntington's disease and Amyotrophic Lateral Sclerosis (also known as Lou Gherig's disease). Additional examples of neurodegenerative disorders and diseases that can be treated by the invention include but are not limited to Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, Pick's disease, Primary lateral sclerosis, Prion diseases, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and other dementias.

In some embodiments, the neurodegenerative disease being treated is dementia. Dementia is a loss of mental ability severe enough to interfere with normal activities of daily living, lasting more than six months, not present since birth, and not associated with a loss or alteration of consciousness. Dementia is a group of symptoms caused by gradual death of brain cells. Dementia is usually caused by degeneration in the cerebral cortex, the part of the brain responsible for thoughts, memories, actions and personality. Death of brain cells in this region leads to the cognitive impairment that characterizes dementia. This degeneration can be a result of the process of aging. The loss of cognitive abilities that occurs with dementia leads to impairments in memory, reasoning, planning, and personality. The dementia may be a result of the process of aging, or may be a result of a sudden neural injury event. Of the known dementias, Alzheimer's disease (AD) is the most common, followed by vascular or multi-infarct dementia. The brain of a person with AD becomes clogged with two abnormal structures, called neurofibrillary tangles and senile plaques. Neurofibrillary tangles are twisted masses of protein fibers inside nerve cells, or neurons. Senile plaques are composed of parts of neurons surrounding a group of proteins called beta-amyloid deposits. The underlying cause for the development of these structures is unknown. Current research indicates possible roles for inflammation, blood flow restriction, and toxic molecular fragments known as free radicals. Several genes have been associated with higher incidences of AD, although the exact role of these genes is still unknown. Vascular dementia (VD) occurs from decrease in blood flow to the brain, most commonly due to a series of small strokes (multi-infarct dementia). Other cerebrovascular causes include: vasculitis from syphilis, Lyme disease, or systemic lupus erythematosus; subdural hematoma; and subarachnoid hemorrhage. Because of the usually sudden nature of its cause, the symptoms of vascular dementia tend to begin more abruptly than those of aging or Alzheimer's dementia. Symptoms may progress stepwise with the occurrence of new strokes. Unlike AD, the incidence of vascular dementia is generally lower after age 75. Other conditions that may cause or be involved in the development of dementia include: AIDS; Parkinson's disease; Lewy body disease; Pick's disease; Huntington's disease; Creutzfeldt-Jakob disease; brain tumor; hydrocephalus; head trauma; multiple sclerosis; prolonged use of alcohol or other drugs; vitamin deficiency in thiamin, niacin, or $B_{12}$; hypothyroidism; and hypercalcemia.

A mammal suffering from neural cell injury or death stemming from stroke can also be treated in accordance with the methods of the invention. Stroke is a type of cardiovascular disease that generally involves the interruption of blood flow to and/or within the brain. The interruption of blood flow can be due, for example, to a blockage or rupture of an artery or vessel. The blockage typically occurs from a blood clot. As a result of the interruption of blood flow, the brain does not receive a sufficient amount of blood.

A mammal suffering from trauma to the nervous system can also be treated in accordance with the methods of the invention. As described above, trauma of the CNS or PNS include, but are not limited to, spinal cord injuries, spinal cord lesions, other CNS pathway lesions, as well as injuries to the PNS, such as injuries to a nerve or neuron of the PNS and axon damage resulting in demyelination of the PNS. Such trauma can arise from either physical injury or disease. A mammal suffering from a trauma of the CNS or PNS can be treated in accordance with the methods of the present invention. For example, spinal cord injury refers to any damage to the spinal cord. The damage typically results in loss of function, such as mobility or feeling. Damage to the spinal cord can occur, for example, as a result of a physical trauma (e.g., car accident, gunshot, fall, etc.) or a disease (e.g., polio, spina bifida, Friedreich's Ataxia, etc).

In the case of spinal cord injury, the injury can be, for example, a complete or incomplete injury to the spinal cord. Complete injury typically refers to a lack of function (e.g., no sensation and no voluntary movement) below the site of injury. Both sides of the body are typically affected. Alternatively, the injury may be an incomplete injury to the spinal cord. An incomplete injury generally refers to some function below the site of injury. For example, a person with an incomplete injury may be able to move one limb more than another, may be able to feel parts of the body that cannot be moved, or may have better function on one side of the body than the other, etc. Additional injuries, traumas, and insults include, for example, epilepsy-related brain damage; infectious disease, such as bacterial or viral meningitis and meningo-encephalitis, or prion diseases; poisoning with neurotoxic compounds; and radiation-induced brain damage.

In one embodiment, the HIF PHD-inhibiting or ATF4-inhibiting compound is administered to the patient in such a manner that the composition does not specifically target particular tissue or cells of the body. The composition can be administered non-specifically by, for example, injection into the blood stream. In another embodiment, the composition is administered to the patient in such a manner that the composition selectively targets particular tissue or cells of the body. The composition can be made to selectively target particular tissue or cells within a mammal by, for example, administering the composition in a localized manner at the site of target tissue or cells (for example, by injection into target tissue or cells). In an alternative embodiment, the composition can be made to selectively target particular tissue or cells within a mammal by administering the composition non-locally or locally, and including in the composition a selective targeting agent (bound or otherwise associated with the compound) that selectively targets certain tissues or certain cells of the body (e.g., by employing an antibody targeting agent). The tissue being treated can be, for example, tissue of the heart, kidneys, liver, bone marrow, pancreas, spleen, skin, lungs, nerves (particularly of the peripheral nervous system), eyes (e.g., retina), muscles, and brain, and any other tissue that may suffer from, or be at risk for, hypoxic damage.

In order to realize the therapeutic effect of HIF PHD or ATF4 inhibition, the compound is administered in a therapeutically effective amount. The effective amount of the compound to be administered can be readily determined by those skilled in the art, for example, during pre-clinical trials and clinical trials, by methods familiar to physicians and clinicians. As is well known in the art, the dosage of the active ingredient(s) significantly depends on such factors as the extent and type of neural damage, method of administration, size of the patient, and potential side effects. In different embodiments, depending on these and other factors, a suitable dosage of the active ingredient may be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, per 50 kg, 60 kg, or 70 kg adult, or a dosage within a range bounded by any of the foregoing exemplary dosages. Depending on these and other factors, the composition is administered in the indicated dosage by any suitable schedule, e.g., once, twice, or three times a day for a total treatment time of one, two, three, four, or five days, and up to, for example, one, two, three, or four weeks. The indicated dosage may alternatively be administered every two or three days, or per week. Alternatively, or in addition, the composition is administered until a desired change is evidenced.

An effective amount of a compound useful in the methods of the present invention, preferably in a pharmaceutical composition, may be administered to a mammal in need thereof by any of a number of well-known methods for administering pharmaceutical compounds. For example, the compound may be administered systemically or locally. The compound may also be administered orally, intravenously, intranasally, intramuscularly, subcutaneously, or transdermally. Other routes of administration include intracerebroventricular or intrathecal routes, wherein intracerebroventricular refers to administration into the ventricular system of the brain and intrathecal refers to administration into the space under the arachnoid membrane of the spinal cord. Intracerebroventricular or intrathecal administration may be preferred for those diseases and conditions that affect the organs or tissues of the central nervous system.

The compounds useful in the methods of the invention may also be administered to a patient by sustained release. As known in the art, sustained release administration is a method of drug delivery to achieve a certain level of the drug over a particular period of time. The level typically is measured by serum or plasma concentration. A description of methods for delivering a compound by controlled release can be found in, for example, international PCT Application No. WO 02/083106, the contents of which are herein incorporated by reference in their entirety. Other controlled release agents are described, for example, in U.S. Pat. Nos. 5,567,439; 6,838,094; 6,863,902; and 6,905,708, the contents of which are also herein incorporated by reference.

Examples have been set forth below for the purpose of illustration and to describe the best mode of the invention at the present time. However, the scope of this invention is not to be in any way limited by the examples set forth herein.

EXAMPLES

Secondary injury from ICH has been attributed to hemin, a breakdown product of hemoglobin (from lysed red blood cells). To investigate the mechanisms of hemin toxicity to neurons in vitro, this experiment exposed primary cortical neurons, immortalized hippocampal neuroblasts (HT22 cells), and immortalized striatal neuroblasts (Q7 cells) to hemin for 24 hours. As expected, a dose dependent loss in viability as measured by MTT reduction or LIVE/DEAD assay in all three cell types was observed. Hemin treatment of primary neurons at the LD50 (50 µM) resulted in a time-dependent increase in heme-oxygenase expression and iron content suggesting that hemin is taken up into neurons and metabolized. To examine whether iron-dependent HIF PHD enzymes can be modulated to protect neurons from hemin-induced toxicity, this experiment examined structurally diverse inhibitors of the HIF PHDs: desferoxamine, cyclopirox, and dihydroxybenzoic acid. Co-treatment of neurons with hemin with structurally diverse HIF PHD inhibitors inhibited hemin-induced neuronal death in all three cell types examined. Previous studies established that while DFO and DHB can inhibit HIF PHD enzymes and stabilize HIF, only DFO can reduce iron content in neurons. These findings suggested that PHD inhibition and not metal chelation is the on target effector of DFO in protecting against hemin toxicity. To test this notion further using a chemical biological approach, the protective effects of cyclopirox, a HIF PHD inhibitor, and a cyclopirox analog with no PHD inhibitory activity but with similar metal binding affinity to cyclopirox were compared. As expected, only the cyclopirox analog with PHD inhibitory activity was neuroprotective. Moreover, the neuroprotection did not correlate with a significant change in total cellular iron levels as measured by inductively coupled plasma optical emission spectroscopy.

While DFO, DHB, and cyclopirox target the HIF PHDs and prevent hemin-induced toxicity, HIF PHDs belong to a superfamily of more than 60 2-oxoglutarate dependent dioxygenases. Some of these other family members are known to be inhibited by low molecular weight inhibitors of the HIF PHDs and so these other members might account for the neuroprotection herein observed. To address whether selective molecular reduction of the oxygen sensing PHD enzymes is sufficient to improve outcomes following ICH, the experiment conditionally reduced PHD1, PHD2, and PHD3 expression simultaneously in the striatum of adult mice using dual injections of AAV8-Cre Recombinase (AAV8-Cre) and mice with homozygous floxed alleles of all three enzymes. The experiment chose to reduce all three HIF PHD enzymes because prior studies in liver have shown that triple knockouts are required to stabilize HIF and drive Epo synthesis. The experiment focused on the striatum because this is where most intracerebral hemorrhages occur. The experiment used a floxed tdTomato reporter to verify that a dual injection of the AAV-8-CRE virus induced recombination mediolaterally in the striatum, which corresponded to the center of the hemorrhagic stroke induced in these mice. The results confirmed that AAV8-CRE but not AAV8-GFP injection into floxed mice two weeks prior to inducing ICH resulted in a significant reduction in message for each of the HIF PHDs and significant induction of canonical HIF target genes vascular endothelial growth factor and erythropoietin. As VEGF is produced primarily in neurons by HIF-1α, and Epo by HIF-2α in glial cells, these data suggest that the AAV8s transduce both neurons and glia. The experiment then induced ICH in wt and PHD deficient mice using collagenase, an enzyme that is known to induce hemorrhage via disruption of the basal lamina of blood vessels. Collagenase causes an evolving bleed that fills the striatum leading to cell death and persistent behavioral deficits. Consistent with the in vitro studies using chemical inhibitors of HIF PHDs, molecular reduction of the three HIF PHDs concurrently resulted in improved somatosensory function after injury at 3 and/or 7 days, depending on the task examined. Of note, this behavioral improvement occurred in the absence of changes in edema formation or hematoma size, suggesting that the salutary effects of HIF PHD inactivation occurred downstream of basal lamina disruption and striatal hemorrhage.

Molecular inactivation studies involving the HIF PHDs provide an important in vivo proof of concept of the viability of these oxygen sensing enzymes as a therapeutic target for ICH. However, as most ICH is spontaneous or acquired in those not known to be at high risk, it is difficult to imagine a practical prophylactic strategy for this illness. Rather, a specific, drug-like molecule which targets the HIF PHDs would be ideal as this would facilitate inhibition of the target post-injury.

To identify HIF PHD inhibitors suitable for testing in ICH, the experiment first sought to identify which of the known HIF PHD inhibitors could penetrate the blood brain barrier to inhibit HIF PHD activity in the CNS. To monitor HIF PHD activity dynamically, the experiment utilized mice that had previously been engineered to ubiquitously express the oxygen degradation domain (ODD) of HIF-1α fused to firefly luciferase. The ODD domain contains proline 402 and 564, which are hydroxylated by the HIF PHDs to degrade HIF-1 or the ODD-luciferase. Accordingly, these mice have been used previously to track HIF PHD activity in diverse organs in vivo using in vivo bioluminescence imaging. Unexpectedly, it was herein found that canonical HIF PHD inhibitors, DFO, DHB and cyclopirox failed to increase ODD-luciferase activity in the brain. The failure of these agents to inhibit HIF PHDs could not be attributed to a lack of intrinsic inhibitory activity of these drugs as they induced the ODD-luciferase activity in cell based assays in parallel to being injected intraperitoneally into mice.

In an effort to overcome these unexpected negative results, the experiment focused on a novel small molecule, branched oxyquinoline inhibitor of the HIF PHDs for its ability to inhibit the HIF PHDs and activate adaptive responses to hypoxia in a cell based assay. The compound, referred to herein as "adaptoquin", has the following structure:

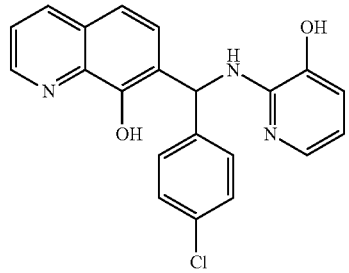 [SMILES: Oc1cccnc1NC(c1ccc(Cl)cc1)c1ccc2cccnc2c1O]

In silico modeling predicted that adaptoquin should bind to the active site of HIF PHDs, and this was verified by the ability of adaptoquin to inhibit the ability of recombinant HIF prolyl hydroxylase 2 to hydroxylate an HIF peptide as monitored by non-denaturing mass spectrometry. In contrast to non-selective HIF PHD inhibitors, such as DFO and DHB, it was herein found that adaptoquin (30 mg/kg) could significantly increase ODD-luciferase levels and activity as monitored by in vivo bioluminescence imaging in brain. To verify that the changes in light in the brain reflect parenchymal changes in ODD-luciferase levels rather than increases in changes in skin or dural ODD-luciferase, ODD-luciferase activity was measured normalized to total protein in lysates from distinct brain regions using a luminometer. An increase in activity in response to adaptoquin treatment was observed. Stabilization of ODD luciferase in the brain was correlated with increased message levels of p21 waf1/cip1, a known HIF-1 regulated gene. These results suggest that adaptoquin (30 mg/kg) penetrates distinct regions of the brain with equal avidity to inhibit the oxygen sensing prolyl hydroxylase domain enzymes and drive HIF-dependent gene expression.

To determine whether HIF PHD inhibition after ICH can improve behavioral outcomes, 30 mg/kg of adaptoquin was delivered to the peritoneum of mice two hours following the injection of collagenase into the striatum. An identical dose of adaptoquin (30 mg/kg) was given daily for seven days. To verify that adaptoquin does not inhibit collagenase activity in the brain, hematoma size was measured at 24 hours in wt and adaptoquin treated mice and found no difference between treated and untreated groups. Even though adaptoquin did not affect hematoma size at 24 hours, it was found that it did decrease edema at three days. In addition to reducing edema, adaptoquin also resulted in behavioral improvement. Mice with striatal hemorrhage show a preference to turn ipsilaterally due to deficits in their weight balancing movements of the limbs contralateral to injury; this preference is significantly normalized by treatment with adaptoquin as measured by the corner turn task. Another somatosensory impairment (e.g., tape removal task) showed significant improvement with adaptoquin treatment at 1 and 3 days post ICH. Improvements in behavior induced by adaptoquin were associated with a reduction in the number of degenerating neurons in the striatum in the hematoma as well as perihematomal area.

To determine whether adaptoquin could ameliorate outcomes using a distinct model of ICH in a distinct species, adaptoquin was tested it (30 mg/kg, intraperitoneal) in a model of autologous blood infusion in rats. Autologous blood infusion causes a narrower slit like lesion in the striatum than collagenase, but results in motor impairments out beyond 30 days. Adaptoquin (30 mg/kg) was administered two hours after autologous blood infusion and then daily for seven days. The drug resulted in no significant changes in temperature, body weight, and glucose levels, but did result in significant improvements in percent correct on a single pellet reaching task at later (23-25 days) time points after ICH. Together, the mice and rat data show that adaptoquin can effectively improve functional recovery of sensorimotor or motor outcomes following ICH in collagenase or autologous blood models.

These molecular deletion and pharmacological inhibition studies supported HIF PHDs as targets for therapy post ICH, but left unanswered the mechanism by which adaptoquin could abrogate neuronal death. A first prediction of the model was that adaptoquin enhances functional recovery without affecting total brain iron levels. Total iron levels were monitored in brain sections from vehicle- and adaptoquin-treated (30 mg/kg) mice seven days following ICH. Despite clear improvements in outcomes in the adaptoquin-treated mice, there were no differences in apparent distribution or total iron or zinc levels as measured by x-ray fluorescence spectroscopy. The data suggest that adaptoquin works downstream or parallel to iron accumulation in the brain, which is consistent with a model in which a specific metalloenzyme, the HIF prolyl hydroxylases, are inhibited to prevent damage and enhance functional recovery.

The canonical target for HIF PHD inhibition is the stabilization of HIF-1α, leading to induction of a genetic adaptive response to hypoxia. To assess whether HIF-1α (or HIF-2α) were required for the protective effects of HIF PHD inhibition, the effect of selective HIF deletion on protection from hemin toxicity induced by structurally diverse HIF PHD inhibitors in hippocampal neuroblasts was examined. Reduction of HIF-1α protein using a retroviral shRNA failed to influence hemin-induced toxicity or protection by structurally diverse HIF PHD inhibitors. Similar results were obtained with an shRNA to HIF-2α. Together, these results suggest that HIF PHD inhibition can protect against hemin-induced death independent of the HIF pathway.

To probe the mechanism of adaptoquin-induced neuroprotection, the study moved its attention to a well established model of oxidative stress in neurons induced by glutamate. Like hemin induced toxicity, oxidative glutamate toxicity is abrogated by forced expression of GPX4 (Alim et al., unpublished observations). However, oxidative glutamate toxicity has a much longer window before cells are committed to die (eighteen hours), facilitating analysis of primary events involved in cell death and protection. A detailed dose response and therapeutic window study was performed with adaptoquin in mouse cortical neurons exposed to glutamate or the glutamate analog, homocysteate. As a result, it was found that adaptoquin could lead to complete protection against oxidative death at 1 micromolar when added up to 16 hours after glutamate (or HCA) addition. To probe the mechanism of this potent, delayed protection, a microarray transcriptomics study was performed using RNA from neuronal cultures that had been exposed to glutamate (or HCA) for 16 hours with vehicle, as well as non-protective (100 nM) and protective doses of adaptoquin (1 μM). Protective, but not protective doses of adaptoquin reduced expression of a host of genes induced by oxidative stress including Tribbles homolog 3, methylene tetrahydrofolate reductase, the Xc-transporter, and stanniocalcin-2 hormone glycoprotein. Notably, expression of these genes and cell death are significantly reduced when ATF4 is molecularly deleted. Quantitative PCR confirmed that protective doses of adaptoquin significantly reduces expression of ATF4 dependent genes, including Trib3, MTHFR2, SCL7A11, and STC2. Statistical analysis of gene networks modulated by protective concentrations of adaptoquin revealed a significant correlation.

While there have been shown and described what are at present considered the preferred embodiments of the invention, those skilled in the art may make various changes and modifications which remain within the scope of the invention defined by the appended claims.

What is claimed is:

1. A method for treating a patient suffering from mild traumatic brain injury, the method comprising administering to said patient an effective amount of a HIF prolyl-4-hydroxylase inhibiting compound having the following general formula:

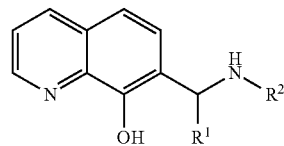

wherein:
$R^1$ is a phenyl ring optionally substituted with a halogen atom or methyl group; and
$R^2$ is a pyridine ring optionally substituted with an —$OR^4$ group, wherein $R^4$ is hydrogen atom or methyl.

2. The method of claim 1, wherein said HIF prolyl-4-hydroxylase inhibiting compound inhibits ATF-4.

3. The method of claim 1, wherein said mild traumatic brain injury is associated with intracerebral hemorrhage.

4. The method of claim 1, wherein said HIF prolyl-4-hydroxylase inhibiting compound decreases edema.

5. The method of claim 1, wherein said patient exhibits somatosensory, sensorimotor, or motor improvement after treatment with said HIF prolyl-4-hydroxylase inhibiting compound.

6. The method of claim 1, wherein said HIF prolyl-4-hydroxylase inhibiting compound has the following structure:

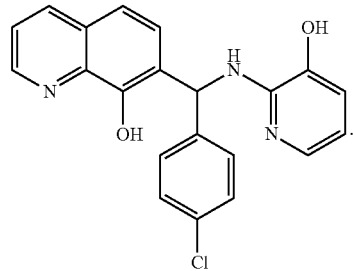 [SMILES: Oc1cccnc1NC(c1ccc(Cl)cc1)c1ccc2cccnc2c1O]

7. The method of claim 1, wherein said mild traumatic brain injury is neurotoxic-induced.

8. The method of claim 1, wherein $R^1$ is a phenyl ring optionally substituted with a halogen atom.

9. The method of claim 1, wherein $R^2$ is a pyridine ring optionally substituted with an OH group.

* * * * *